(12) United States Patent
Dodge

(10) Patent No.: US 8,414,928 B2
(45) Date of Patent: Apr. 9, 2013

(54) METHODS FOR THE GENERATION OF CARTILAGE-LIKE MATERIAL BY MECHANICAL LOADING

(76) Inventor: George R. Dodge, Philadelphia, PA (US)

( * ) Notice: Subject to any disclaimer, the term of this patent is extended or adjusted under 35 U.S.C. 154(b) by 1396 days.

(21) Appl. No.: 11/951,943

(22) Filed: Dec. 6, 2007

(65) Prior Publication Data

US 2009/0148876 A1   Jun. 11, 2009

Related U.S. Application Data

(60) Provisional application No. 60/868,889, filed on Dec. 6, 2006.

(51) Int. Cl.
*C12N 5/00* (2006.01)
(52) U.S. Cl.
USPC .......................... 424/548; 424/93.7; 435/383
(58) Field of Classification Search .................. None
See application file for complete search history.

(56) References Cited

U.S. PATENT DOCUMENTS 6,528,052 B1 * 3/2003 Smith et al. .................. 424/93.7

OTHER PUBLICATIONS

Miyanishi et al, Tissue Engineering, Jul. 2006, vol. 12, No. 6, pp. 1419-1428.*
Jakob et al, Journal of Cellular Biochemistry, 2001, vol. 81, pp. 368-377.*

* cited by examiner

*Primary Examiner* — Allison Ford

(57) ABSTRACT

A cartilage-like biomaterial is bioengineered by using a self-aggregating suspension cell culture with hydrostatic mechanical force without the use of a scaffold or foreign matrix for cell attachment during culture. The cells in suspension culture may be preconditioned prior to application of the hydrostatic mechanical force, such as hydrostatic pressure, for a period of time in the range of about 1 week to about 10 weeks. The cartilage-like biomaterial shares critical structural, phenotype, and functional characteristics with native, intact cartilage tissue.

36 Claims, 27 Drawing Sheets

Panel A  Panel B

Panel A  Panel B

Primers used span 144-659
Natural Perlecan = 515 bp:  Miniperl = 346 bp

Primer 1 spans the splice site
Primer 353 would be spliced out in Miniperl

Panel D

Panel E

Panel F

Panel G

Panel A

Panel B

METHODS FOR THE GENERATION OF CARTILAGE-LIKE MATERIAL BY MECHANICAL LOADING

CROSS-REFERENCES TO RELATED APPLICATIONS

This application claims priority to and benefit under 35 U.S.C. §119(e) to provisional application No. 60/868,889, filed Dec. 6, 2006, the disclosure of which is herein expressly incorporated by reference in its entirety.

BACKGROUND

1. Field of the Invention

The invention generally relates to use of a suspension culture of cells followed by a period of culture under a hydrostatic load to promote chondrogenesis or osteogenesis without the use of a scaffold or foreign matrix.

2. Related Art

Osteoarthritis is a debilitating joint disease that causes pain and dysfunction. It is characterized by the degeneration of articular cartilage, and affects over 20 million people nationwide. Clinical and research studies are currently striving to understand the disease progression of osteoarthritis and develop improved methods of treatment. Attempts are being made to repair, regenerate, replace, and relieve the pain caused by osteoarthritis.

Exemplary methods of treatment for osteoarthritis currently considered are osteochondral transplantation, microfracture surgery, and tissue engineering. Osteochondral transplantation consists of removing a healthy full depth bone plug from an area that experiences low loads and subsequently press fitting the plug into a hole cut in the damaged location. Although osteochondral transplantation endures over the short-tem, the long-term performance of this technique has not yet been observed. For example, it has not yet been determined if moving tissue from a low-weight bearing area to a high-weight bearing location will ultimately lead to degeneration resulting from mechanical overloading.

In microfracture surgery, several small holes in the range of about 0.5 mm to about 1.0 mm in diameter are drilled into the subchondral bone beneath an area of damaged articular cartilage. Subsequently, blood and bone marrow (which contains stem cells) seep out into the drilled holes creating a blood clot that ultimately produces a material called fibrous cartilage. Although this technique has been used in young patients and athletes and has resulted in pain relief in about 75% of patients and improved joint functionality, the procedure has several limitations. For example, the procedure is less effective in older and overweight patients and the long-term results of the repair have not been characterized.

Alternatively, repair tissue that has mechanical and biological characteristics similar to native cartilage may be engineered and surgically implanted into a patient. Here, cells such as chondrocytes, may be cultured and used to replace the damaged region of cartilage within the patient with a healthy, phenotypically similar material. There are a multitude of choices of scaffolds, cells, signaling molecules, and culture techniques, which may be considered, each of which may present unique complicated biological and biomechanical design problems. Moreover, there are many disadvantages associated with the use of frequently used scaffold matrix materials that include collagen, fibrin, alginate, agarose, and hyluronan such as bio-incompatibility, the presence of foreign body cell-reactions, and biodegradability. Additionally, chondrocytes grown in these ways for even short periods of time begin to de-differentiate and eventually take on a fibroblastic phenotype.

It can be seen from the foregoing discussion that existing techniques for treatment of osteoarthritis have many limitations associated with them such as lack of characterization of the long-term effects, bio-incompatibility, and biological and biomechanical design issues. Thus, there is a need for improved methodologies to engineer repair tissue that has mechanical and biological characteristics similar to native cartilage.

SUMMARY OF THE INVENTION

The invention provides a method for inducing chondrogenesis or osteogenesis using a suspension culture of cells followed by a period of culturing the cells under a load without the use of a scaffold or foreign matrix thereby increasing the biocompatibility for cartilage replacement. Bioactive agents, such as growth factors, polypeptides, vitamins, nutrients, and minerals, may be added to the suspension culture to further enhance or promote chondrogenesis or osteogenesis.

According to one aspect of the invention, a method for producing a cartilage-like biomaterial is provided. The method may include culturing cells having a density of at least about $1 \times 10^6$ cells/ml in a culture media at conditions suitable for growth in suspension, maintaining the cells in suspension for a period of time without the use of any physical support for cell attachment, applying a mechanical force at an effective pressure for a period of time, and forming a cartilage-like biomaterial. The method may further include seeding cells in a culture apparatus containing the culture media prior to said culturing step. Moreover, the method may include preconditioning the cells for a period of time prior to applying the mechanical force. Preconditioning may be for a time period in the range of about 1 week to about 10 weeks, and specifically for about 8 weeks the cartilage-like biomaterial expresses collagen Type II. Moreover, the cartilage-like biomaterial may minimally express or have undetectable levels of collagen Type I.

The cells may be derived from a source selected such as autologous tissue, allogenic tissue, and xenogenic tissue. The cells may be undifferentiated cells such as mesenchymal stem cells, embryonic stem cells, and pluripotent adult stem cells. The undifferentiated cells maybe cultured in a chondrogenic media or complete media. The cells may be differentiated cells such as chondrocytes and may be cultured in a complete media.

The mechanical force may include cyclical dynamic loading, dynamic shearing, and hydrostatic loading. In particular, the hydrostatic loading may be cyclical hydrostatic pressure. The mechanical force may be at a pressure is in a range of about 0.5 MPa to about 1.0 MPa. The mechanical force may be applied intermittently. The mechanical force may be applied about 3 times per week for a time period of about 3 hours. The mechanical force may be applied for a period of time in range of about 1 week to about 10 weeks.

The culture media may be augmented with a chondrogenic factor such as BMP-2, BMP-4, chondrogenic stimulating activity factor (CSA), TGF-$\beta$, IL-1, IL-6, and IL-8, insulin-like growth factor I (IGF-I), fibroblast growth factors (FGF), prostaglandins, vascular endothelial growth factor (VEGF), platelet-derived growth factor (PDGF), perlecan, and miniperl, chondroitin sulfate, glucosamine, glucosamine sulfate, and combinations thereof.

The culture media may be augmented with a biologically active factor such as naphthpquinone, tocopherol and tocotrienol, ergocalciferol and cholecalciferol, ascorbic acid, cyanocolbalamin, folic acid, biotin, pyridoxine, pantothenic acid, niacin, riboflavin, thiamine, and reinoids and carotenoids, and minerals such as iron, calcium, magnesium, zinc, copper, selenium, iodine, chromium, potassium, manganese, glucosamine, glucosamine sulfate, and combinations thereof.

According to another aspect of the invention, a method of producing cartilage-like bio material is provided. The method may include culturing a high density suspension culture of cells without physical support for cell attachment, and applying a hydrostatic load to produce the cartilage-like biomaterial. The hydrostatic load may be applied continuously or intermittently. The hydrostatic load may be applied about 3 times per week for a time period of about 3 hours. The cells may be cultured for a time period in a range of about 1 week to about 10 weeks. The cells may be preconditioned for a time period in the range of about 1 week to about 4 weeks prior to applying the cyclical hydrostatic load to the cells.

The cells may be primary culture cells such as mesenchymal stem cells, embryonic stem cells, pluripotent adult stem cells, and combinations thereof. Alternatively, the cells may be chondrocytes. The cells may be cultured at a density in a range of about $1 \times 10^6$ cells/mL to about $1 \times 10^9$ cells/mL, and specifically about $1 \times 10^6$ cells/mL to about $1 \times 10^8$ cells/mL. The cells in culture may have the capacity to self-aggregate and form a biomass. The density of suspension cells may be in a range of about $1 \times 10^6$ cell/mL to about $1 \times 10^8$ cells/mL.

The cells may be cultured in a chondrogenic medium augmented with a chondrogenic factor. The chondrogenic factor may include BMP-2, BMP-4, chondrogenic stimulating activity factor (CSA), TGF-β, IL-1, IL-6, and IL-8, insulin-like growth factor I (IGF-I), fibroblast growth factors (FGF), prostaglandins, vascular endothelial growth factor (VEGF), platelet-derived growth factor (PDGF), perlecan, and miniperl, chondroitin sulfate, glucosamine, glucosamine sulfate, and combinations thereof.

Another aspect of the invention is directed to a method for producing bone from culture cells. The method may include culturing a high density suspension of culture cells without any physical support for cell attachment, applying a hydrostatic load to the culture cells, inducing osteogenesis, and producing bone. The mechanical force may include cyclical dynamic loading, dynamic loading, dynamic shearing, and hydrostatic loading. The cells may be preconditioned for a time period in a range of about 1 week to about 10 weeks prior to the application of the mechanical force. In particular, the cells may be preconditioned for a period of about 8 weeks. The cells may be undifferentiated cells such as mesenchymal stem cells, embryonic stem cells, and pluripotent adult stem cells.

The cells may be cultured in osteogenic media. The osteogenic may be augmented with an osteogenic factor such as dexamethasone, insulin growth factor 1 (IGF-1), insulin, Wnt family of proteins such as Wnts-1, Wnts-2, Wnts-3, Wnts-3a, Wnts-4, Wnts-5a, Wnts-5b, Wnts-7a, and Wnts-8, bone morphogentic proteins (BMP) such as BMP-2, BMP-4, BMP-6, and BMP-7, vitamin D, thrombospondins, retinoic acid, and calcium.

According to another aspect of the invention, a method for determining an abnormal or normal process in a subject. The method may include obtaining a sample from the subject, assaying for an expression level of miniperl in the sample, and determining whether the expression level of miniperl in the sample varies from a expression level of miniperl in a control sample, where a difference in the miniperl expression level in comparison to the miniperl expression level in the control sample is indicative of the abnormal process in the subject.

The difference in the miniperl expression level in the sample may be increased in comparison to the miniperl expression level in the control sample. The difference in the miniperl expression level in the sample may be decreased in comparison to the miniperl expression level in the control sample. The sample may be a biological sample derived from body fluid, a tissue sample, an organ sample, feces, blood, salvia, and any combination thereof. The normal process is non-pathologic. The abnormal process may be cancer such as breast or lung cancer, and altered development genetic defects.

The expression level of miniperl may be obtained by using a PCR reaction using primer sequences such as SEQ ID No. 1, SEQ ID No. 2, SEQ ID No. 3, SEQ ID No. 4, and SEQ ID No. 5.

Additional features, advantages, and embodiments of the invention may be set forth or apparent from consideration of the following detailed description, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced.

FIG. 13A showing Panels A-C are bar graphs showing the expression of aggregan, decorin, and perlecan in loaded and unloaded samples, respectively. FIG. 13B, Panels D-G are bar graphs showing the relative expression of collagen type II, collagen type IIA, COMP, and CD44 in loaded and unloaded, respectively.

DETAILED DESCRIPTION OF THE INVENTION

Figure 1:
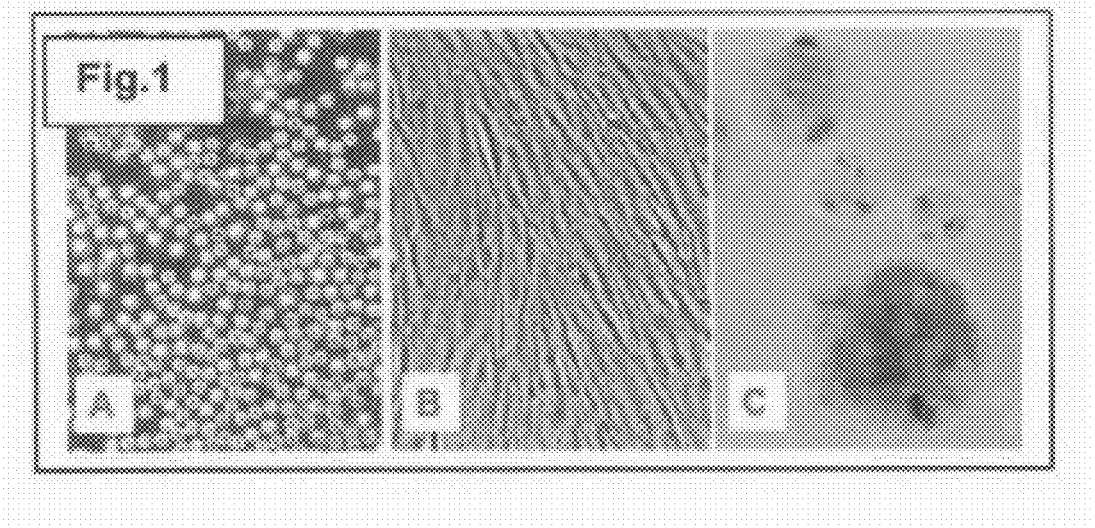
FIG. 1 is a micrograph of the chondrocytes grown in suspension culture. Panel A shows clusters of chondrocytes derived from fresh articular cartilage seed at a density of about $1 \times 10^6$ chondrocytes/mL according to principles of the invention. Panel B shows the appearance of the chondrocyes when attached to the culturing dish. Panel C shows the chondrocytes after 1 week in suspension culture according to principles of the invention.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is be noted that as used herein and in the appended claims, the singular forms "a," "an," and "the" include the plural reference unless the context clearly dictates otherwise. Thus, for example, a reference to "a cell" is a reference to one or more cells and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Accordingly, provided immediately below is a "Definition" section, where certain terms related to the invention are defined specifically for clarity, but all of the definitions are consistent with how a skilled artisan would understand these terms. Particular methods, devices, and materials are described, although any methods and materials similar or equivalent to those described herein can be used in the practice or testing of the invention. All references referred to herein are incorporated by reference herein in their entirety.

DEFINITIONS

CTE is cartilage tissue equivalent
ECM is extracellular matrix
DDMB is dye 1,9-dimethylmethylene blue
DMEM is Dulbecco/Vogt modified Eagle's essential media
GAG is glycosaminoglycan
polyHEMA is poly (2-hydroxyethyl methacrylate)
SD is standard deviation "Chondrogenesis" as used herein, generally refers to the formation or growth of chondrocytes in response to stimuli such as cell culture conditions, load, and administration of an effective amount of an chondrogenic factor.

"Chondrogenic factor" or "chondrogenic inductive factor," as described herein, may include natural or synthetic, recombinant, organic or inorganic chemical or biochemical compound or combination or mixture of compounds, or any mechanical or other physical device, container, influence, or force that can be applied to differentiated or undifferentiated cells to induce and/or promote chondrogenesis or the production of chondrocytes. The chondrogenic factor may be a variety of peptides, e.g., growth factors and related molecules which are able to promote chondrogenesis leading to the formation of cartilage-like biomaterial when administered to the suspension cell culture. Exemplary factors include bone morphogenic protein (BMP) such as BMP-2 or BMP-4, chondrogenic stimulating activity factor (CSA), TGF-β, IL-1, IL-6, and IL-8, insulin-like growth factor I (IGF-I), fibroblast growth factors (FGF), NO, prostaglandins, vascular endothelial growth factor (VEGF), platelet-derived growth factor (PDGF), perlecan, miniperl, and nutraceuticals including without limitation chondroitin sulfate, glucosamine, and glucosamine sulfate.

The term "osteogenic factor" as used herein may include may include natural or synthetic, recombinant, organic or inorganic chemical or biochemical compound or combination or mixture of compounds, or any mechanical or other physical device, container, influence, or force that can be applied to differentiated or undifferentiated cells to induce and/or promote osteogenesis or the production of osteocytes. The osteogenic factor may be a variety of peptides, e.g., growth factors and related molecules which are able to promote osteogenesis leading to the formation of bone when administered to the suspension cell culture. Exemplary factors include glucocortocoids such as dexamethasone, insulin growth factor 1 (IGF-1), insulin, Wnt family of proteins such as Wnts-1, Wnts-2, Wnts-3, Wnts-3a, Wnts-4, Wnts-5a, Wnts-5b, Wnts-7a, and Wnts-8, bone morphogentic proteins (BMP) such as BMP-2, BMP-4, BMP-6, and BMP-7, vitamin D, thrombospondins, retinoic acid, and calcium.

"Cartilage-like biomaterial" or "cartilage tissue equivalent (CTE)," as used herein, generally refers to a three dimensional mass of living mammalian tissue produced primarily by growth in vitro. The cartilage-like biomaterial may include one or more types of cells or tissues. For example, the cartilage-like biomaterial may be made up of chondrocytes alone or stem cells alone or cultured in conjunction with other cell types, such as multipotent adult stem cells such as mesenchymal stem cells, pluripotent adult stem cells, embryonic stem cells, and any various subsets of these cell types. More particularly, cartilage-like biomaterial may include three dimensional tissue which share critical structural, phenotypical, and functional characteristics with intact, native cartilage tissue.

"Mesenchymal stem cells," as used herein is an example of a multipotent adult stem cell that may be found in bone marrow and has the ability to differentiate into several different cell lineages such as osteocytes, chondrocytes, and adipocytes upon activation. Mesenchymal stem cells may be isolated and purified from bone marrow by methods known to those of skill in the art and the methods described herein, infra.

"Mammal," as used herein, includes animals and humans. Thus, when referring to processes such as harvesting tissue from an animal, it is intended that the animal can be a human. Although at times reference may be made herein to "an animal or human," this is not intended to imply that the term "animal" does not include a human.

"Subject," as used herein, includes individuals who require intervention or manipulation due to a disease state, treatment regimen or experimental design. Furthermore, the term "subject" includes animals and humans.

"Autologous," as used herein, generally refers to an autologous cell or tissue that originates or is derived from the recipient.

"Allogenic," as used herein, generally refers to an allogenic cell or tissue that originates from or is derived from a donor of the same species as the recipient.

"Xenogeneic," as used herein, generally refers to a cell or tissue that originates from or is derived from a donor of a different species than the recipient.

"Biologically Active Agent," as used herein, generally refers to any naturally occurring or synthetic compound that is capable of inducing a change in the phenotype or genotype of a cell, tissue, organ or organism when contacted with the cell, tissue, organ or organism. For example, the compound may promote and/or induce chondrogenesis, promote and/or induce osteogenesis, cell survival, cell proliferation, cell differentiation, tissue formation; and may inhibit fibrosis, inflammation, de-differentiation and tumorigenesis. The compounds may be secreted from the cells or exogenous compounds may be added to the cell or tissue culture media so as to supply the compound. The compounds may include, for example, chemical mediators, such as small molecule therapeutics (e.g., peptides), bone morphogenic protein (BMP) such as BMP-2 or BMP-4, chondrogenic stimulating activity factor (CSA), TGF-β, IL-1, IL-6, and IL-8, insulin-like growth factor I (IGF-I), fibroblast growth factors (FGF), NO, prostaglandins, vascular endothelial growth factor (VEGF), platelet-derived growth factor (PDGF), perlecan, miniperl, and nutraceuticals including without limitation chondroitin sulfate, glucosamine, and glucosamine sulfate, glucocortocoids such as dexamethasone, insulin growth factor 1 (IGF-1), insulin, Wnt family of proteins such as Wnts-1, Wnts-2, Wnts-3, Wnts-3a, Wnts-4, Wnts-5a, Wnts-5b, Wnts-7a, and Wnts-8, bone morphogentic proteins (BMP) such as BMP-2, BMP-4, BMP-6, and BMP-7, vitamin D, thrombospondins, retinoic acid, calcium, naphthpquinone, tocopherol and tocotrienol, ergocalciferol and cholecalciferol, ascorbic acid, cyanocolbalamin, folic acid, biotin, pyridoxine, pantothenic acid, niacin, riboflavin, thiamine, and reinoids and carotenoids, and minerals such as iron, calcium, magnesium, zinc, copper, selenium, iodine, chromium, potassium, and manganese.

"Polypeptide," as used herein, refers to a linear series of amino acid residues connected to one another by peptide bonds between the alpha-amino group and carboxy groups of adjacent amino acid residues. Additionally covalent bonds between portions of the peptide are also present to restrain the conformation of the molecule, such as amide and disulfide bonds. When used herein, "protein" also refers to a linear series of amino acid residues connected one to the other as in a peptide. The term "synthetic peptide" means a chemically derived chain of amino acid residues linked together by peptide bonds that is free of naturally occurring proteins and fragments thereof The polypeptides of the invention may be a naturally purified product, or a product of a chemical synthetic-procedure, or produced by recombinant techniques from a prokaryotic or eukaryotic host.

The term "fragments" may include any portion of a peptide or nucleic acid sequence that retain at least one structural or functional characteristic of the subject polypeptide. Nucleic acid sequence fragments are greater than about 60 nucleotides in length, and most specifically includes fragments that are at least about 100 nucleotides, at least about 1000 nucleotides, and at least about 10,000 nucleotides in length.

The term "functional equivalent," as used herein generally refers to a protein or nucleic acid molecule that possesses functional or structural characteristics that are substantially similar to a protein, polypeptide, enzyme, or nucleic acid. A functional equivalent of a protein may contain modifications depending on the necessity of such modifications for the performance of a specific function. The term "functional equivalent" is intended to include the "fragments," "mutants," "hybrids," "variants," "analogs," or "chemical derivatives," of a molecule.

The term "purification," as used herein, generally refers to any process by which proteins, polypeptides, or nucleic acids are separated from other elements or compounds on the basis of charge, molecular size, or binding affinity.

The phrase "substantially purified," or "substantially isolated," as used herein generally includes nucleic or amino acid sequences that are removed from their natural environment, isolated or separated, and are at least about 60% free, specifically at least about 75% free, and most specifically at least about 90% free from other components with which they may be associated with, and includes recombinant or cloned nucleic acid isolates and chemically synthesized analogs or analogs biologically synthesized by systems.

The phrases "conditions suitable for growth" or "appropriate cell culture conditions" for a suitable cell type, as used herein, generally refers to an environment with conditions of temperature, pressure, humidity, mechanical stress, mechanical force, nutrient and waste exchange, and gas exchange that are permissive for the survival and reproduction of the cells. With respect to any particular type of cell, an environment suitable for growth may require the presence of particular nutrients or growth factors needed or conducive to the survival and/or reproduction of the cells. For example, a "chondrogenic media" may be an augmented version of Dulbecco's Modified Eagle's Medium (DMEM) (Invitrogen, Carlsbad, Calif.), which is well known and readily commercially available. The DMEM may be supplemented with 10 µL/mL ITS+ premix (MP Biomedicals Life Sciences, Solon Ohio), 50 µg/mL ascorbic acid, 40 µg/mL proline, 10 ng/mL TGF-β, and 0.1 µg dexamethasone; an osteogenic medium may be DMEM with 10% FBS, 100 units/ml penicillin, 100 µg/ml streptomycin, 2.5 µg/ml amphotericin, 2 mM glutamine, 1% MEM vitamin solution (Invitrogen), 25 mM HEPES buffer, and 50 µg/ml ascorbic acid with 100 nmol/L dexamethasone, 10 mmol/L beta-glycerophosphate, and 0.05 mmol/L L-ascorbic acid; and a control or complete medium may be DMEM with 10% FBS, 100 units/ml penicillin, 100 µg/ml streptomycin, 2.5 µg/ml amphotericin, 2 mM glutamine, 1% MEM vitamin solution (Invitrogen), 25 mM HEPES buffer, and 50 µg/ml ascorbic acid.

"Primary Culture Cells," as used herein, generally refer to cells that are not fully differentiated but may have the capacity to either become more fully differentiated or to give rise to a cell (or cells) that is able to further differentiate. The primary culture cell may be capable of giving rise to one or more different cell types, such as chondrocytes and osteocytes. More particularly, primary culture cells may be cells that either have a native capacity for differentiation into chondrocytes or that the cells may be manipulated into forming chondrocytes. Accordingly, small samples of autologous, allogenic or xenogeneic donor cells may be used for cartilage-like biomaterial of the invention.

"Pre-conditioning," as used herein, generally refers to growing the primary culture cells in media such as chondrogenic media under appropriate cell culture conditions permissive for the reproduction and survival of the cells prior to application of mechanical loading. The suspension cell culture may be pre-conditioned for a duration in the range of about 1 week to about 10 weeks prior to application of mechanical load, and specifically about 8 weeks.

The term "high density cell suspension" as used herein generally refers to seeding the chondrocytes or primary culture cells at a density in a range of about $1\times10^6$ cell/mL to about $1\times10^8$ cells/mL.

The terms "mechanical loading," "mechanical force," "load," and "mechanical stress," as used herein, generally refers to applying a mechanical stress upon a cell in culture and may be used interchangeably throughout the application. The mechanical stress may initiate intracellular signaling, promote cell growth and survival, govern morphology and architecture, and influences metabolic responses. Mechanical loading may include cyclical dynamic loading, dynamic shearing, and cyclical hydrostatic pressure. Specifically, the mechanical stress may include cyclic loading in the range of about 0.1 MPa to about 5 MPa applied for a duration in the range of about 1 hour to about 10 hours at a frequency of about 0.1 Hz. The mechanical force may be applied continuously or intermittently. One skilled in the art may determined the minimum or maximum load as well as to apply the load continuously or intermittently to have the desired effect.

"Self aggregating," as used herein, generally refers to the capacity to self-associate, gather, or cluster into a mass or body and form a matrix.

The cell types that may be used to generate the cartilage-like biomaterial of the invention may include, but are not limited to, chondrocytes, multipotent adult stem cells such as mesenchymal stem cells, pluripotent adult stem cells, and embryonic stem cells. Depending on the application of the cartilage-like biomaterial and the type of cartilage-like biomaterial that is desired, the above types of cells may be used independently or combined with one another. In one embodiment, the cartilage-like biomaterial may be composed of primary tissue isolates from cartilage. Alternatively, cells such as stem cells or mesenchymal stem cells may manipulated to form chondrocytes or osteocytes using the methodology of the invention.

The mesenchymal stem cells isolated and purified as described herein, infra, may be derived, for example, from bone marrow, blood, dermis, synovium, or periosteum. Specifically, the bone marrow may be derived from a number of different sources, including without limitation plugs of femoral head and cancellous bone pieces, obtained from patients during surgery, from aspirated marrow obtained from normal donors and other means known by those of skill in the art.

The invention relates generally to methods and products for use in the field of tissue engineering and replacement tissues. In particular, the invention provides methods for producing a cartilage-like biomaterial by using a self-aggregating suspension cell culture and mechanical force without the use of a scaffold or foreign matrix for cell attachment. Moreover, the suspension cell culture may be grown in a media augmented with bioactive factors, chondrogenic factors, osteogenic factors, or a combination thereof. The cells in suspension culture may be preconditioned prior to application of the hydrostatic mechanical force, such as hydrostatic pressure, for a period of time in the range of about 1 week to about 10 weeks. The cartilage-like biomaterial produced by the methods of the invention share critical structural, phenotype, and functional characteristics with native, intact cartilage tissue.

The methodology of the invention is unique in that it is not a pellet culture-based system, which is based on high cell density and gravity and does not require the use of a scaffold or foreign matrix for cell attachment such as agarose or alignate. Since the methodology of the invention does not require the use of a scaffold or foreign matrix for cell attachment, the bio-compatibility of the resultant cartilage-like biomaterial is greatly improved and therefore, more suitable for use in cartilage repair or replacement applications.

Accordingly, in one embodiment of the invention, the cartilage-like biomaterial may be implanted into a subject for the treatment of conditions involving tissue damage or dysfunction in accordance with standard surgical procedures. For example, degenerative joint diseases such as osteoarthritis, chondromalacia, and osteonecrosis and cartilage and bone defects arising from congenital defects and/or trauma. Additionally, damage to non-weight bearing cartilage arising from congenital defects, abnormalities, and/or trauma may also be repaired (e.g., ear and nose). In particular, the cartilage-like biomaterial may be implanted directly into, for example, areas having cartilage damage during surgery. In one embodiment, osteoarthritis may be treated by surgically placing the cartilage-like biomaterial in the damaged cartilage region. After implantation, integration between the transplanted biomaterial and the host tissue may occur thereby repairing the defect. Such a placement would help to re-establish healthy, functional cartilage in the patient. Additionally, the cartilage-like biomaterial may be shaped according to the configuration needed for the desired repair location such as the ear or nose. In another embodiment, the cartilage-like biomaterial may be coated with a factor such as a chondrogenic or osteogenic factor to enhance or integrate the cartilage-biomaterial with the surrounding tissue prior to implantation in a subject or the tissue surrounding the implanted cartilage-like biomaterial in the subject may be treated with such a factor. The cells of the implanted cartilage-like biomaterial may be derived from allogenic, autologous or xenogeneic donor cells and/or tissues.

In an additional embodiment, the cartilage-like biomaterial may be used in basic research for testing and characterizing pharmacologically active compounds. The use of human or animal tissue-equivalents in vitro to test the safety, efficacy, and mechanism of action of potential therapeutic agents is clearly desirable, especially since current methods of analysis fall short. In addition, studying human cartilage equivalents could dramatically expand the current understanding of joint biology and pathology, and specifically cartilage and bone cell biology. In general, the cartilage-like biomaterial of the invention may be produced according to the methods described below.

The methodology of the invention is directed to inducing chondrogenesis or osteogenesis using a suspension culture under mechanical load with or without the presence of bioactive agents and/or chondrogenic factors and without an scaffold or foreign matrix for cell attachment during culture to produce a tissue-engineered biomaterial with a cartilage-like phenotype. The mechanical stress applied during culture may initiate intracellular signaling, promote cell growth and survival, govern morphology and architecture, and influences metabolic responses.

The mechanical loading may include cyclical dynamic loading, dynamic shearing, and cyclical hydrostatic pressure. In a particular embodiment, the mechanical force applied to the suspension culture is cyclical hydrostatic pressure that may be applied continuously or intermittently. The cyclical hydrostatic loading may be applied at a pressure in the range of about 0.1 MPa to about 5 MPa at a frequency of about 0.1 Hz for a single session or for multiple sessions of loading. For example, a session may include applying force about 3 hours for about 3 times per week. However, one skilled in the art would appreciate the amount or duration of time required to achieve the desired effect.

Prior to application of the mechanical load, the suspension culture cells may be placed in any suitable vial with a flexible membrane inset into the cap in order to transmit force and then placed in a pressure chamber. For example, the vial may be a 1.5 ml cryotube tops having ¼ inch holes to allow transmission of pressure. Flexible impermeable membranes may be placed between the cryotube tops before being screwed into place. This is one example of a device that may be utilized in the invention, however, one skilled in the art would appreciate that any number of devices and designs may be implemented.

In another embodiment, prior to application of mechanical load, the suspension culture cells may be preconditioned in conditions suitable for growth, such as in chondrogenic media for a time period in a range of about 1 week to about 10 weeks. Preconditioning cells prior to loading may increase positive response of the suspension cells to the mechanical load by reducing stress upon the cells that the loading regimen may cause.

According to one embodiment, a high concentration or density of primary culture cells or chondrocytes may be cultured in dishes (e.g., 24-well dishes) coated with poly 2-hydroxyethyl methacrylate (polyHEMA) or any other suitable compounds to prevent the cells from attaching to the plastic substrate and remain in suspension. While in suspension, the cells have the capacity to self-aggregate and rapidly form a mass that increases over time. Chondrocytes produced according to this embodiment retain their cartilage specific phenotype. That is, the chondrocytes do not de-differentiate and express type I collagen, which is characteristic of the undesirable fibroblastic phenotype.

According to another embodiment of the invention, the chondrocytes or primary culture cells are seeded into the culture dishes coated with polyHEMA at a density in a range of about $1 \times 10^5$ cells/mL to about $1 \times 10^9$ cells/mL, and specifically in a range of about $1 \times 10^6$ cells/mL to about $1 \times 10^8$ cells/mL. When chondrocytes derived from fresh articular cartilage were seeded at about $1 \times 10^6$ chondrocytes/mL (FIG. 1, Panel A) they rapidly formed clusters, and, in about 1 week, exhibited the characteristics demonstrated in FIG. 1, Panel C. These clusters continued to be biosynthetically active and, when sectioned, have a typical cell to matrix ratio of normal adult articular cartilage. FIG. 1, Panel B shows the appearance cells when they were allowed to attach to the non-polyHEMA-coated cell plates after about 1 week in culture. As shown in FIG. 1, Panel B the attached cells have a fibrotic appearance and do not have a cell to matrix ratio of normal adult articular cartilage.

Figure 2:
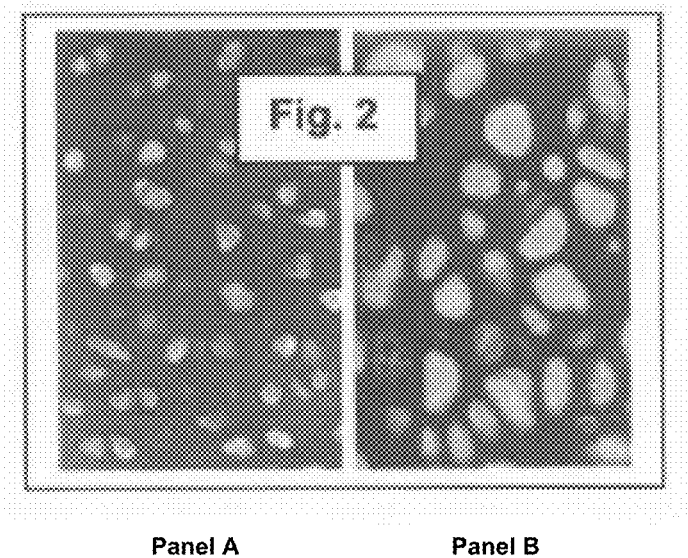
FIG. 2 is a micrograph comparing chondrocytes after about 10 weeks of culture seeded at a density of about $1 \times 10^7$ chondrocytes/mL and natural cartilage. Panel A is natural porcine femoral cartilage. Panel B shows chondrocytes after about 10 weeks of culture seeded at a density of about $1 \times 10^7$ chondrocytes/mL according to principles of the invention exhibiting a cell-to-matrix ratio similar to the natural cartilage in Panel A.

When the chondrocytes were seeded at higher densities, such as greater than about 1×10⁷ chondrocytes/mL, the chondrocytes formed a single mass and after about 10 weeks in culture, appeared very similar to the cell-matrix ratio of natural cartilage (FIG. 2). FIG. 2, Panel A is natural porcine femoral cartilage, and FIG. 2, Panel B is the cartilage-like biomaterial of the invention grown for about 10 weeks at about 2×10⁷ chondrocytes/mL in polyHEMA-coated dishes and stained with Alcian blue. The staining intensities and magnification are not comparable in FIG. 2, Panels A and B since these sections were stained at different times. These figures are presented for the purpose of demonstrating the cell-to-matrix parallel that the cartilage-like biomaterial has to normal cartilage. A mass forms when chondrocytes from all cartilage were tested, including neonatal and adult human and porcine, young or old bovine, and equine-derived chondrocytes (data not shown). Differences between the cell sources lie only in the speed in which the cartilage-like biomaterial forms. The younger chondrocytes form the cartilage-like biomaterial the most rapidly.

Figure 3:
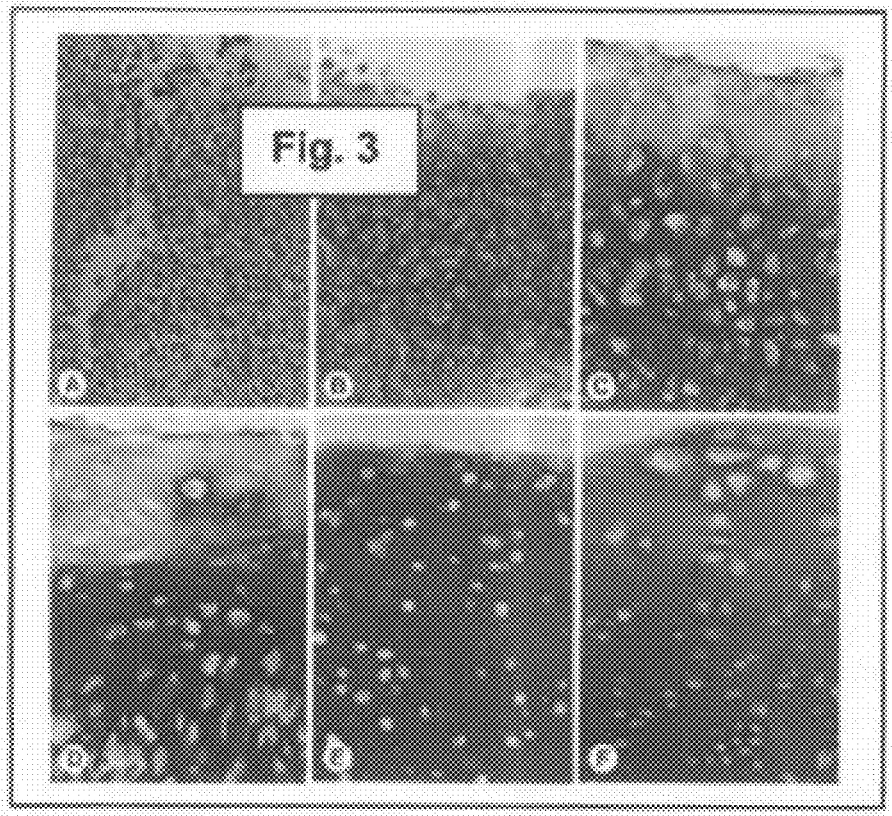
FIG. 3 shows a panel of micrographs of tissue sections obtained by principles of the invention stained with Alcian blue from porcine cartilage-like biomaterial generated in culture over 1 week (Panel A), 2 weeks (Panel B), 3 weeks (Panel C), 4 weeks (Panel D), 5 weeks (Panel E), and 10 weeks (Panel F).

FIG. 3 shows a panel of micrographs of sections stained with Alcian blue from porcine cartilage-like biomaterial generated in culture over 1, 2, 3, 4, 5, and 10 weeks (FIG. 3, Panels A-F, respectively). Remarkably, as early as only 1 week, a noticeable mass is formed and there is evidence of proteoglycan (note that the culture began as a single cell suspension). By week 2, the mass can be picked up and is noticeably cartilage-like in appearance. Over a 10-week culture period, the mass increased to more than about 6 grams and the cells proliferated in the beginning, but by about 4 weeks, leveled off and became more biosynthetically active. The cartilage-like biomaterial formed in as little as 3 weeks in cultures of about 1×10⁸ cells/60 mm dish, which resulted in about a 20 mm diameter cartilage-like biomaterial; in cultures of about 2×10⁷ cells/15 mm well resulted in about a 10 mm diameter. The thickness in either situation varied in the range of about 1 mm to about 3 mm.

Figure 4:
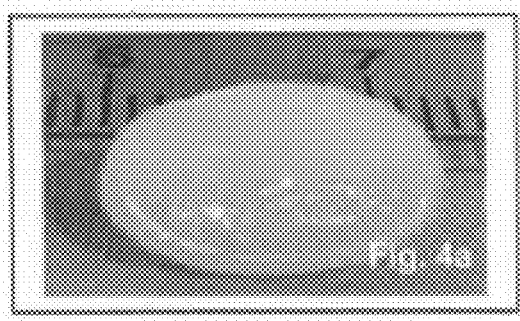
FIG. 4 is a photograph of the cartilage-like biomaterial cultured by the one embodiment of the invention.
Figure 4:
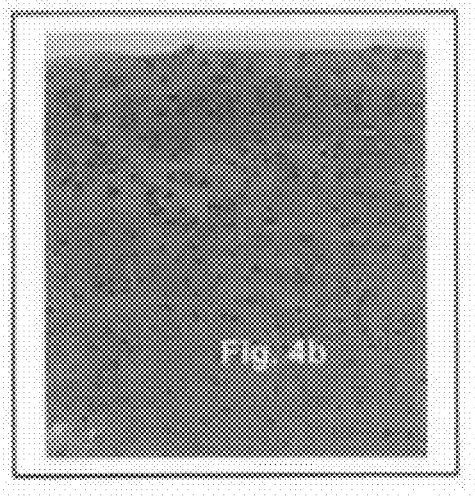
Figure 5:
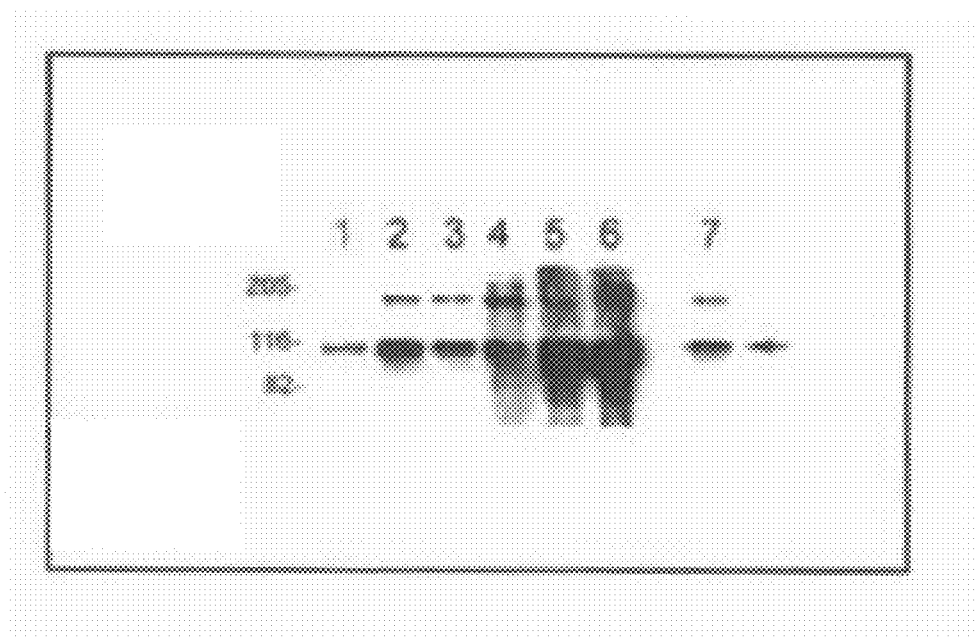
FIG. 5 is a photograph of a Western blot showing an increase in type II collagen present in tissue cultured according one embodiment of the invention. Lane 1 is an extract after 1 week of culturing, Lane 2 is an extract after 2 week of culturing, Lane 3 is an extract after 3 week of culturing, Lane 4 is an extract after 4 week of culturing, Lane 5 is an extract after 5 week of culturing, and Lane 6 is an extract after 10 week of culturing. Lane 7 is a purified pepsin-treated bovine II collagen as a standard.

An example of a cartilage-like biomaterial grown in cultures of about 2×10⁷ cells/15 mm well for about eight weeks is shown in FIG. 4, Panel A. Grossly, it appears white, opaque, and cartilage-like. The increase in tissue weight and architecture, as seen by histochemistry (FIG. 4, Panel B), was paralleled by a marked increase in the expression of type II collagen as detected by Western blotting using an anti-bovine type II collagen antibody (Southern Biotechnologies, Birmingham, Ala.), which cross-reacts with porcine type II collagen. As can be seen in FIG. 5, there is an increase in type II collagen present in the tissue over 10 weeks. Lanes 1, 2, 3, 4, 5, and 6 represent equivalent aliquots of extracts from about 1, 2, 3, 4, 5, and 10 weeks, respectively. Lane 7 is a purified pepsin-treated bovine II collagen as a standard. These data showed that the increased size and weight and the more cartilage like architecture is, in part, due to an increase in biosynthetic activity of the important and characteristic collagen of cartilage, type II.

In a further embodiment of the invention, a biologically active agent may be added to the suspension culture at a time and amount as determined by one skilled in the art to promote and/or induce chondrogenesis, promote and/or induce osteogenesis, cell survival, cell proliferation, cell differentiation, tissue formation; and may inhibit fibrosis, inflammation, de-differentiation and tumorigenesis. The molecules may include, for example, vitamins such as naphthpquinone, tocopherol and tocotrienol, ergocalciferol and cholecalciferol, ascorbic acid, cyanocolbalamin, folic acid, biotin, pyridoxine, pantothenic acid, niacin, riboflavin, thiamine, and reinoids and carotenoids, and minerals such as iron, calcium, magnesium, zinc, copper, selenium, iodine, chromium, potassium, manganese, bone morphogenic proteins (BMP) such as BMP-2. BMP-4, BMP-6, and BMP-7, chondrogenic stimulating activity factor (CSA), TGF-β, IL-1, IL-6, and IL-8, insulin-like growth factor 1 (IGF-I), fibroblast growth factors (FGF), prostaglandins, vascular endothelial growth factor (VEGF), platelet-derived growth factor (PDGF), perlecan, and miniperl, nutraceuticals including without limitation chondroitin sulfate, glucosamine, and glucosamine sulfate, glucocortocoids such as dexamethasone, insulin growth factor 1 (IGF-1), insulin, Wnt family of proteins such as Wnts-1, Wnts-2, Wnts-3, Wnts-3a, Wnts-4, Wnts-5a, Wnts-5b, Wnts-7a, and Wnts-8, vitamin D, thrombospondins, retinoic acid, and calcium.

In another embodiment of the invention, a osteogenic factor may be added to suspension primary cell culture or to the suspension chondrocyte cell culture to promote or enhance osteogenesis. Exemplary osteogenic factors include glucocortocoids such as dexamethasone, insulin growth factor 1 (IGF-1), insulin, Wnt family of proteins such as Wnts-1, Wnts-2, Wnts-3, Wnts-3a, Wnts-4, Wnts-5a, Wnts-5b, Wnts-7a, and Wnts-8, bone morphogentic proteins (BMP) such as BMP-2, BMP-4, BMP-6, and BMP-7, vitamin D, thrombospondins, retinoic acid, and calcium.

In yet a further embodiment of the invention, a chondrogenic factor may be added to suspension primary cell culture or to the suspension chondrocyte cell culture to promote or enhance chondrogenesis. Exemplary chondrogenic factors include bone morphogenic protein (BMP) such as BMP-2 or BMP-4, chondrogenic stimulating activity factor (CSA), TGF-β, IL-1, IL-6, and IL-8, insulin-like growth factor I (IGF-I), fibroblast growth factors (FGF), prostaglandins, vascular endothelial growth factor (VEGF), platelet-derived growth factor (PDGF), perlecan, miniperl, and nutraceuticals including without limitation chondroitin sulfate, glucosamine, and glucosamine sulfate.

The chondrogenic factor, perlecan, is a key member of the growing number of proteoglycans that have both structural and functional roles in a variety of tissues. Perlecan is a large heparan sulfate proteoglycan with a core protein of about 467 kDa that is found in all basement membranes and a variety of other specialized tissues including the synovium, cartilage, and developing bone. Recently, it has been shown that mice lacking the perlecan gene have severe chondroplasia and chondro-osseous defects. Mutations in the perlecan gene have also been identified as responsible far a condition called dyssegmental dysplasia in humans, which may indicate that this proteoglycan has a critical role in the development and functional characteristic of cartilage and bone.

Perlecan is a complex molecule made of up five distinct domains with only domain I being unique. The other four share homology with low density lipoprotein receptor, the N-terminal of laminin A and B short arms, the neural cell adhesion molecule, N-CAM, and the globular domain of the C-terminus of laminin A including the two EGF-repeat sequences, respectively. Due to this complex structure, perlecan has been implicated in a variety of biological functions such as the binding and delivery of growth factors and nutrients affecting such processes as cell adhesion, cellular metabolism, and angiogenesis.

Figure 6A:
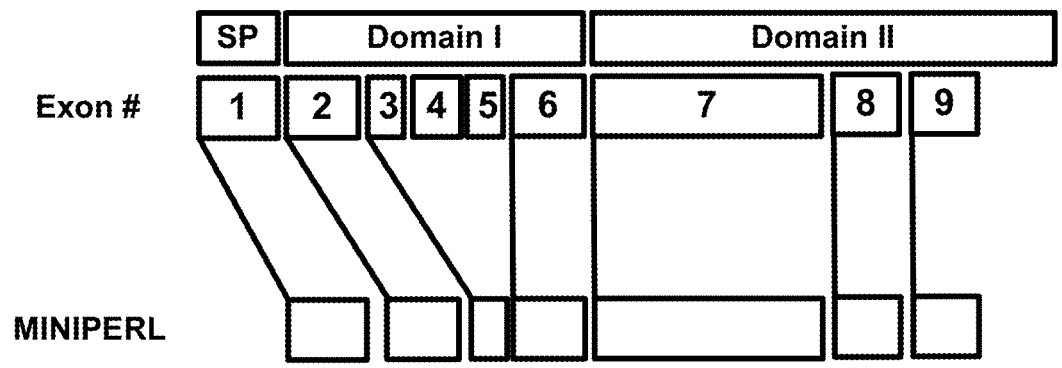
FIG. 6 is a photograph of a cDNA gel following real-time PCR performed on miniperl and perlecan transcripts. Panel A shows perlecan after PCR amplification using primer spanning nucleotides 144-659. Panel B shows PCR amplification using the splice site at high annealing temperature of human chondrocyte RNA.
Figure 6B:
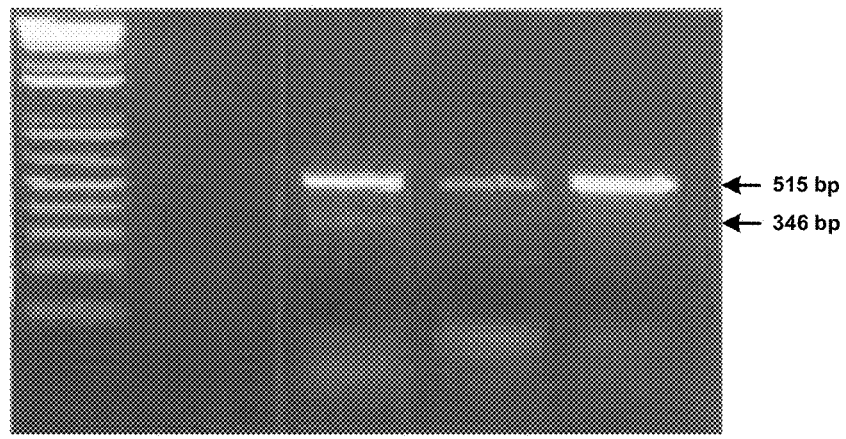
Figure 6C:
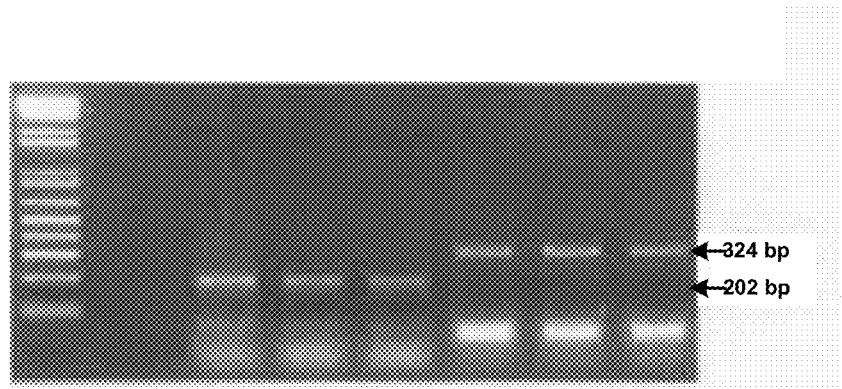

An alternative spliced form of perlecan was discovered by the inventor that involves domain I, which is unique to perlecan and important in chondrogenesis. Due to a frame shift, it results in a drastically shorter protein with perlecan-like characteristics and is referred to as miniperl (GenBank accession number AF479675). Miniperl is a protein with 239 amino acids, where 60 amino acids are identical to perlecan and 179 amino acids are novel, and preserves the glycosaminoglycan (GAG) motifs. Miniperl has exons 4 and 5 of domain I spliced out, which results in a frame shift and a stop codon at position 1050 (numbered according to submission GenBank accession M85289.1). FIG. 6, Panel A (FIG. 14A) shows the schematic of the splicing event, and FIG. 6, Panel B shows the presence of the alternative transcript in the RNA of three separate fresh human chondrocyte preparations.

Figure 7:
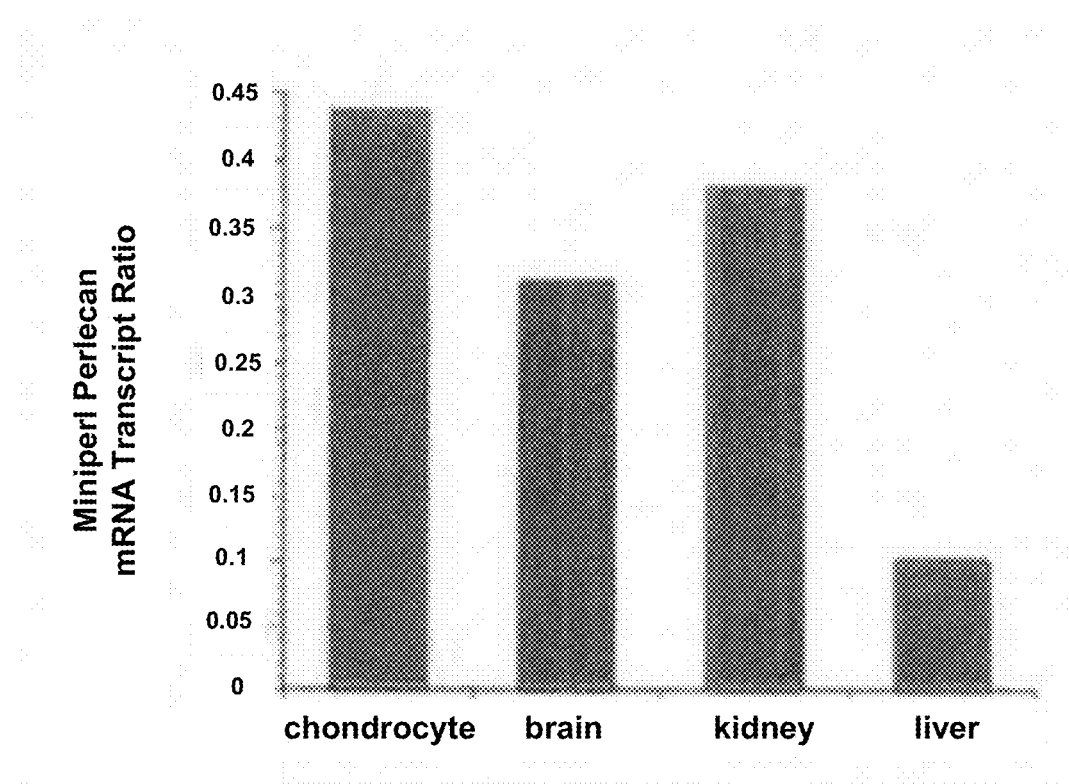
FIG. 7 is a graph showing the ratio of miniperl to perlecan mRNA transcripts in equine tissue determined by real-time PCR.

PCR was performed for miniperl and perlecan transcripts using a primer (FIG. 6, Panels B and C) that spans the splice site, and a primer (FIG. 6, Panels B and C) that is inside the spliced-out portion of miniperl. Using real-time PCR, the ratio of miniperl to perlecan was determined as shown in FIG. 7. The ratio of miniperl:perlecan varies in both cell type and tissue RNA preparations tested, which is between a half and one tenth as abundant as perlecan. Miniperl was consistently higher in cartilage and chondrocytes than the other tissue/cell source tested.

According to alternate embodiment of the invention, miniperl may be used as a marker of normal processes such as chondrogenesis or abnormal processes. Miniperl has been identified in most tissues and may be a marker of cancer such as lung and breast, for example. Accordingly, the an increase or decrease in the expression of miniperl may be a marker of disease and/or a marker for stages in development of pathology of a disease or disorder such as tumor aggressiveness, tumor growth, and/or tumor proliferation. Miniperl expression may be tested for using a PCR reaction using specific primers that would only amplify miniperl. The primers used and method are as follows using perlecan primers that span the region of domain I. A standard PCR reaction was performed at high annealing temperatures (about 66° C.) to increase specificity and to compensate for the high GC content of the region.

A primer designed around nucleotide 144 (5' GTGAC-CCATGGGCTGAGGGCATA 3' (SEQ ID No. 1)) ("Primer No. 144") and a primer designed around nucleotide 659 (5' GGGCACTGTGCCCAGGCGT 3' (SEQ ID No. 2)) ("Primer No. 659") (primer number designation is based on the gene sequence location as found in accession no. AF479675) produced a natural perlecan PCR product of about 515 base pairs (bp) and a miniperl product of about 346 bp (FIG. 6, Panel B). A natural perlecan specific primer designed around nucleotide 353 (5' TCGCTCCATCGAGTACAGCC 3' (SEQ ID No. 3)) ("Primer No. 353") and designed around nucleotide 677 (5' GCAGGCTCTTGGGAACTGGGG 3' (SEQ ID No. 4)) ("Primer No. 677), only amplified one 324 bp PCR product (FIG. 6, Panel C). Primers designed around nucleotide 1, which spans the splice site (5' ACTTCCAGATGGG-GAGCTGGATGG 3' (SEQ ID No. 5)) ("Primer No. 1") and Primer No. 677 (SEQ ID No. 4) only generated miniperl (FIG. 6, Panel C). Primer No. 353 (SEQ ID No. 3) only amplified perlecan because that region of the sequence is spliced out in miniperl. Primer No. 1 (SEQ ID No. 5) only amplified miniperl because amplification would be prevented in the perlecan mRNA because of the large intervening sequence residing in the middle of the primer region.

Alternatively, the expression level of miniperl may be determined in a subject by obtaining a sample assaying the sample using an antibody that has the capacity to detect miniperl and/or a fragment thereof.

Without further elaboration, it is believed that one skilled in the art using the preceding description can utilize the invention to the fullest extent. The following examples are illustrative only, and not limiting of the disclosure in any way whatsoever.

EXAMPLES

Specific Example 1

Effects of Loading on CTEs

In this example, specimens were exposed to hydrostatic pressure and compared with culture-time-matched unloaded control specimens. Using the suspension culture method according to principles of the invention, primary chondrocyte CTEs were developed without the addition of scaffold or foreign material is demonstrated. Moreover, the resultant CTEs resembled normal cartilage and responded to physiologically relevant hydrostatic load by significantly increasing expression of cartilage molecules.

Cartilage Source

Femoral head, condyle epiphyseal, and articular cartilage were removed under sterile conditions from neonatal Yorkshire pigs within 2 hours of death. They were obtained from a commercial breeding farm at the New Bolton Center in Kennett Square, Pa. The Institutional Animal Care and Use Committee (IACUC) reviewed the procedure and exempted it from full IACUC review, since the tissue was discarded from a commercial supplier of animals for consumption.

Chondrocyte Isolation and Culture Model

The cartilage was held in Dulbecco's minimum essential medium (DMEM) (Mediatech, Herndon, Va.) at 4° C. until isolation of chondrocytes was possible. Soft tissue and perichondrium were removed, and the cartilage was isolated from the growth plate before cutting it into small pieces of about $3mm^3$.

The articular cartilage was processed through enzymatic digestion with bacterial collagenase initially at 2 mg/ml for 1 hour followed by 0.5 mg/ml overnight in DMEM containing 10% fetal bovine serum (FBS) (Gibco-BRL, Grand Island, N.Y.), 100 units/ml of penicillin, 100 μg/ml of streptomycin, amphotericin B 2.5 μg/ml 2, mM glutamine, 1% MEM vitamin solution (Invitrogen) overnight at 37° C. The cells were washed twice by centrifugation resuspended with fresh DMEM containing 10% FBS medium. The average yield was about $4.0 \times 10^7$ cells/gram of tissue.

The isolated chondrocytes were plated at a density of about $2 \times 10^7$/well/1 ml in a 24-well plate treated with polyHEMA (or "low cluster plate", Becton Dickinson). The culture medium used was DMEM containing 10% FBS, 100 units/ml of penicillin, 100 μg/ml of streptomycin, 2 mM glutamine, 1% MEM vitamin solution (GIBCO, BRL), and 50 μg/ml of ascorbic acid and was changed every 2-3 days. The cells were incubated at 37° C. in 5% $CO_2$; during loading periods the device was also warmed to 37° C.

Hydrostatic Loading of CTEs

The CTEs were cultured in this manner for 1 week prior to the beginning of the loading experiment to form a mass. Within 1 week, a mass of cells and matrix was formed that could be moved from the well without perturbation. Eight CTE specimens were separated into two groups, the unloaded control group and the loaded group. The control specimens remained under the same culture conditions, while the loaded CTE specimens were placed in a four-well plate containing DMEM with 10% FBS, 100 units/ml of penicillin, 100 μg/ml of streptomycin, 2 mM glutamine, 1% MEM vitamin solution (GIBCO, BRL), and 50 μg/ml of ascorbic acid (freshly made). The cultures were moved to vials (1.0 ml cryovials) that previously had the top drilled open and replaced with a flexible membrane. Vial caps were modified replacing the solid surface with a flexible membrane that allowed for the transmission of hydrostatic pressure and protected the CTE from contamination. The sealed tubes were then placed in a pressure chamber (25 cm×20 cm×10 cm) and filled with hydraulic fluid. The chamber was sealed, and the remaining air within the chamber was extracted. The chamber was contiguous with a 2.5 kip hydraulic piston, which was mounted onto a materials testing machine (Instron Corp., Canton, Me.). The testing machine crosshead compressed the piston and loaded the chamber and the cultures. Cyclical loading in the range of about 0.5 MPa to about 5.0 MPa was applied for about 3 hours three times a week, for three weeks at a frequency of about 0.1 Hz. To maintain the temperature, the chamber was warmed during the procedure to 37° C. by sitting atop a controlled heating block.

After each loading session, specimens were decompressed, removed from the chamber, and transferred from the vials to the storage wells with fresh medium. The loaded CTEs were kept in an incubator between loading sessions. During the 3-week experiment, the medium was replaced for both the loaded and control specimens after each loading session. Spent medium was saved prior to each loading session and stored frozen (about −20° C.) with protease inhibitors [1×] (PI) (Roche) until later analysis of collagen and proteoglycan expression changes.

Mechanical Analysis of CTE

Following the completion of the hydrostatic loading regimen, both loaded and control CTE specimens underwent biochemical and mechanical analysis. One-dimensional confined compression incremental stress relaxation testing was performed to quantify the material properties of the tissue. Mechanical testing was performed using a high resolution materials testing machine (Instron Corp., Canton, Me.) and a 10 N load cell (Instron Corp., Canton Me.) with load and displacement accuracy of about ±0.04 N and about ±0.02 μm, respectively. Two 5 mm diameter plugs were punched from both the loaded and unloaded control CTEs. These specimens were placed in a confined compression chamber bathed in phosphate buffer solution (PBS, Invitrogen Corp., Grand Island, N.Y.) and allowed to swell for 30 minutes to achieve an unloaded equilibrium state.

The test applied an initial tare load of about 0.08 N applied for 15 minutes followed by five 7.5% compressive strain increments conducted at a rate of 0.25 μm/s. Following each strain increment, the displacement was held constant for 1400 seconds to allow the samples to reach equilibrium. Time, displacement, and load data were collected during each experiment at a sampling rate of 0.1 Hz. Stress versus time plots were generated from the data. A material model using finite deformation biphasic theory {Mow, 1980 #381}, which assumes the solid phase of cartilage to be hyperelastic and isotropic {Holmes, 1990 #359} was used determine the equilibrium aggregate modulus ($H_{ao}$) and permeability ($k_o$).

Hydroxyproline Assay

Levels of hydroxyproline were determined relative to other amino acids as an estimation of collagen content (in chondrocyte CTEs the major collagen being collagen type II). A hydroxyproline assay was conducted on both medium and sample tissue. Medium was removed and saved in 25× Complete Protease Inhibitor (Roche Diagnostics). Sample medium was acidified with equal volume 12 N hydrochloric acid (HCl). Tissue samples were diced using a razor blade and suspended in 6 N HCl. The samples were gassed with nitrogen and sealed tightly. Hydrolysis took place at about 110° C. for 24 hours. Samples were thoroughly mixed and purified to amino acids using Poly-Prep Pre-filled Chromatography Columns with $H^+$ cation exchange resin (Bio-Rad). Amino acids were eluted with 4 M ammonium hydroxide ($NH_4OH$). The samples were dried on a speed-vac and resuspended in 20 nM HCl.

The entire sample was then run on a high performance liquid chromatography column (HPLC). Peaks were identified for hydroxyproline and other common amino acids for standardization. The ratio of hydroxyproline to these other amino acids was used to measure relative collagen in each sample.

Glycosaminoglycan (GAG) Assay

GAGs were measured in medium and CTEs. Frozen tissue samples were thawed and papain digested in a solution consisting of 150 μg/ml type III papain, 20 mM sodium phosphate, 1 mM EDTA, and 2 mM dithiothreitol at pH 6.8. Samples were digested at 60° C. for 24 hours. After vortexing the samples and centrifugation to remove particulate, samples were adjusted to pH 8 by addition of 5 M NaOH (4 μl NaOH/ml sample) and heated to 55° C. for 2 hours to dissolve insoluble DNA.

GAG and DNA were quantified separately, and the ratio was used to determine a quantity of GAG produced per cell. GAG content was determined in each sample (tissue or medium) using the dimethyl methylene blue binding assay, (Blyscan BioScan, Belfast, Ireland). Fifty μl of the digest or medium was analyzed following the procedure as described by the manufacturer. Chondroitin 4-sulfate purified from bovine trachea was used to produce a standard curve (0-5 μg) (BioScan, Belfast, Ireland). Triplicates were averaged from both the DNA and GAG assay and expressed as GAG/DNA.

DNA Assay

DNA was measured using the Picogreen reagent (Molecular Probes, Eugene, Oreg.). Briefly, 100 μl digest was added in triplicates to a microplate. A standard curve was prepared with a 2.0 μg/ml and assayed in triplicates (0.06-2.0 μg/ml). Picogreen reagent was prepared in low light at a 1:200 dilution in 1× TE buffer, added at equal volume (100 μl), and mixed. After 5 minutes, the plate was read at 485/20 excitation and 530/25 emission on a CytoFluor fluorometer (PerSeptive Biosystems, Stafford, Tex.).

RNA Isolation

Total RNA was isolated using the following procedure. For chondrocyte CTEs, snap-frozen samples were homogenized using a freezer mill (Spex LLC, Metuchen, N.J.). The frozen powder was quickly transferred to a centrifuge tube and solubilized with 1 ml of Trizol Reagent (Invitrogen). Following the manufacturer's protocol, total RNA was isolated and solubilized in 60 μL DEPC-treated water.

The concentration of total RNA was determined by a spectrophotometer. The $OD_{260}$ was used to determine RNA concentration with $OD_{260}:OD_{280}$ values between 1.5 and 2.0. To remove DNA contamination and fragments of RNA, the entire volume of RNA from each sample was applied to a silica membrane spin column (Qiagen, Valencia, Calif.). The samples then were on-column digested with RNase-free DNase-I before being eluted (Qiagen, Valencia, Calif.). Using oligo (dT) and random hexamer primers reverse transcriptase, 1 μg total RNA was reverse transcribed into cDNA in 40 μl reactions (iScript, BioRad). The RT protocol consisted of 5 minutes at 25° C., 50 minutes at 42° C., followed by 5 minutes at 85° C. in an icycler (BioRad, Hercules, Calif.).

Quantitative PCR

Levels of mRNA were determined using specific primers for genes of interest (CD44, collagen types I and II, aggrecan, perlecan, decorin, COMP, iNOS). From cDNA prepared as described above, real time PCR was performed using an ABI 7900 Real time workstation. Each reaction was performed in triplicate and consisted of 35 µl 2×SYBR Green with ROX internal reference dye (iTaq, Bio-Rad), 2.1 µl forward and reverse primers, 3.5 µl template, and RNAse-free water up to 70 µl. Using the robotic automatic pipettor, each mixture was distributed into 20 µl triplicates. Forty cycles were carried using the following parameters: 95° C. for 30 seconds, various optimized annealing temperature for 30 seconds, extension at 72° C. for 40 seconds. Primers were designed to span introns, had products equal to or less than about 350 base pairs, and were optimized prior to use for efficiency.

Housekeeping genes (HKG) (GAPDH or eEF1) were used for relative expression studies to normalize the expression to cDNA loading quantity. A calibrator positive control (CPC) sample was used for $\Delta\Delta C_T$ expression for each gene of interest (GOI). The formulas used to determine relative expression were as follows:

1. Average $C_T^{GOI}$–Average $C_T^{HKG}=\Delta C_T^{SAMPLE}$

2. $\Delta C_T^{SAMPLE}-\Delta C_T^{CPC}=\Delta\Delta C_T$

3. Average and SEM of biological replicate $\Delta\Delta C_T$s taken

4. $2^{-\Delta\Delta C_T}$=Relative expression

Results were confirmed by standard RT-PCR using the iTaq DNA Polymerase kit (Bio-Rad). Analysis was performed by densitometry, and relative expression was consistent with the real time data. Statistical analysis was performed using single factor analysis of variance (ANOVA). Differences were considered significant at p<0.05.

Measurement of Nitric Oxide

Samples of medium were saved from all time points in culture and stored at −20° C. in protease inhibitors. The presence of NO in medium would indicate an unfavorable response to load. To measure production of NO by our CTEs in response to loading, we employed the use of the Griess reagent (Sigma, St. Louis, Mich.). The Griess reagent measures nitrite, the stable end product of NO. NO was measured by established methods that have been previously used {Das, 1997 #3979; Lee, 2002 #2702} {Sakurai, 1995 #3991}. To prevent formation of a precipitate, GAG chains present in some medium were precipitated out of the medium prior to the assay by application of protamine sulfate (10 mg/ml) (Sigma). Briefly, samples were vortexed and centrifuged at 10,000 rpm for 10 minutes. Supernatant was added to equal volume Griess reagent and read on a microplate at 540 nm after 15 minutes.

The CTEs generated from control and loaded chondrocyte cultures were analyzed for their biomechanical, biochemical, and molecular characteristics. Gross appearance of the biomass formed in unloaded or loaded samples was similar and took a disc-like shape that with time appeared more whitish and opaque. Chondrocyte CTEs were cut and half used for RNA isolation. No macroscopic differences were evident in either control or loaded cultures, and they all were in the range of about 1.5 cm to about 2.0 cm in diameter and in the range of about 1 mm to about 2 mm thick. Microscopically it was evident that the chondrocytes maintained their round cell shape, and, over the 3-week culture period, there was an increasing accumulation of ECM.

In order for a CTE to have any chance of suitability for clinical use, it needs to share biomechanical properties with natural cartilage. The mean aggregate modulus, permeability, and model correlation coefficient ($R^2$) of the 3-week control samples and 3-week loaded samples are listed in Table 2, below.

| GROUP (n = 4) | $H_{ao}$ (kPa) Mean (±SD) | $k_o \times 10^{-13}$ (m$^4$/Ns) Mean (±SD) | $R^2$ Mean (±SD) |
|---|---|---|---|
| CONTROL | 15.1 (0.86) | 10.52 (9.4) | 0.96 (0.02) |
| Load | 21.1 (3.85) | 1.27 (0.56) | 0.97 (0.003) |

Figure 8:
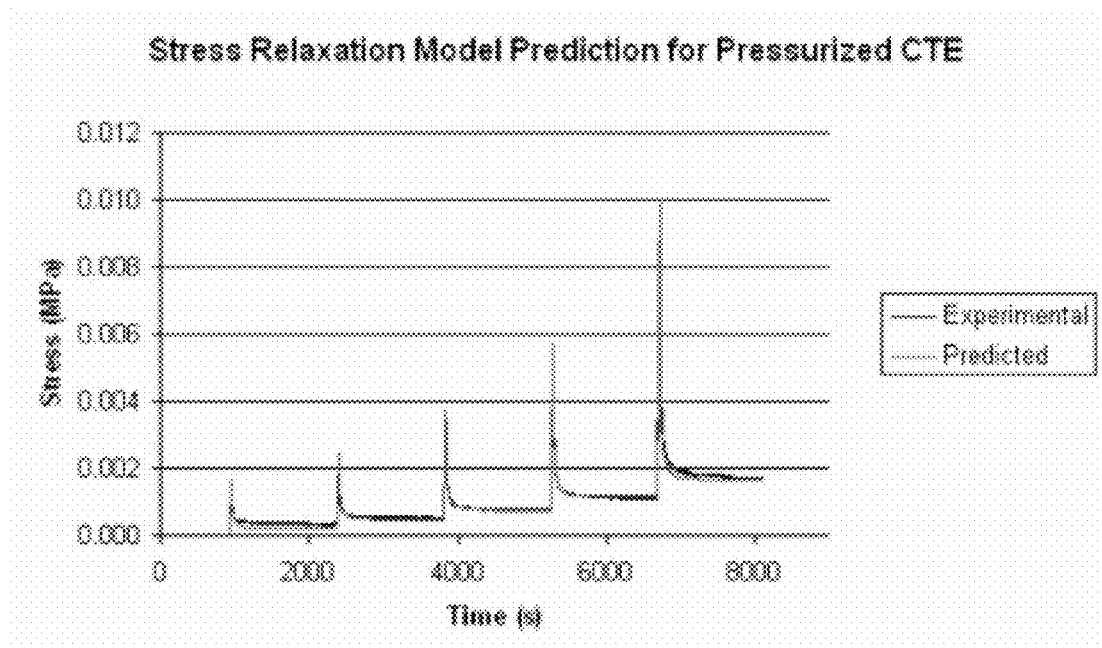
FIG. 8 is a graph showing a sample model prediction versus the actual experimental stress relaxation data of a loaded CTE specimen accoding to principles of the invention. The model accurately predicts the stress relaxation response with a correlation coefficient ($R^2$) of >0.95.
Figure 9:
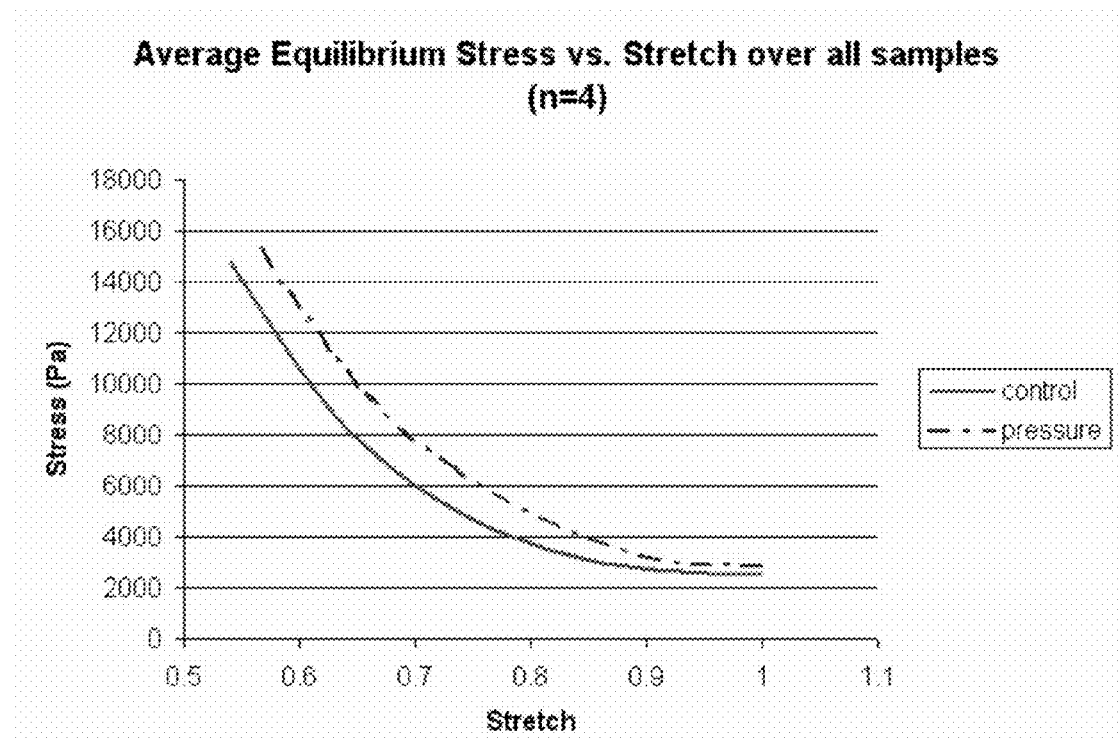
FIG. 9 is a graph showing the average equilibrium stress versus stretch response for both control and loaded specimens according to principles of the invention. The shift in the curve is indicative of an increase in strength of the loaded CTE.

An example of the fit of experimental data to theoretical prediction was shown for the stretch relaxation experiment for a 3-week loaded specimen is shown in FIG. 8. The model accurately predicted the experimental data for all CTE specimens, with a correlation coefficient ($R^2$) greater than 0.95. The mean equilibrium stress versus stretch of the control and hydrostatically loaded samples is depicted in FIG. 9. The aggregate modulus of the 3-week control and loaded specimens regimen were about 15.1 kPa (0.86 SD) and about 21.1 kPa (3.85 SD), respectively, indicating about a 40% increase. The permeability was found to be about $10.5\times10^{-13}$ m$^4$/Ns ($9.4\times10^{-13}$ SD) for the control specimens and about $1.27\times10^{-13}$ m$^4$/Ns ($0.56\times10^{-13}$ SD) for the loaded specimens for about an 88% decrease.

Figure 10:
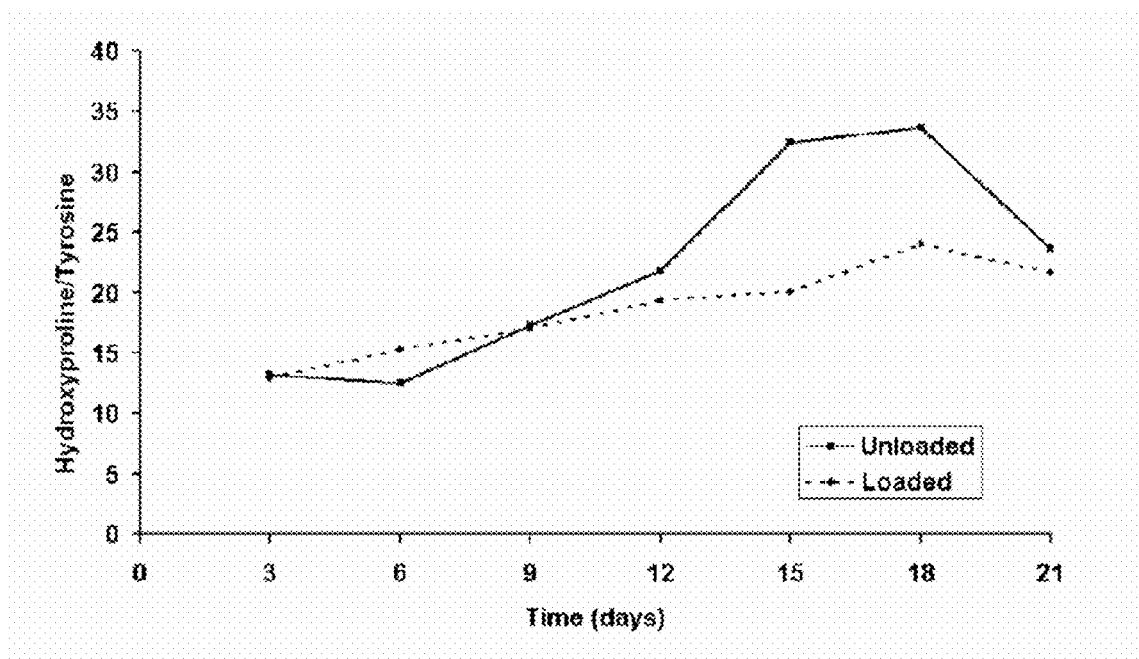
FIG. 10 is a graph showing secreted collagen over time by CTE measured by HPLC HyPro. The effects of loading result in less collagen being released into the medium. Loading increased the incorporation of collagen type II into the ECM.

The effects of loading chondrocyte CTEs were assessed after various loading durations (1-3 weeks of loading after 1 week in suspension culture). Medium was removed every 2 days for the duration of the study (21 days). Medium and CTEs (at study's end) were then assessed for hydroxyproline content by hydrolysis followed by HPLC. Hydroxyproline, relative to other amino acids, was used as a measure of collagen content. Collagen was secreted into the medium more in control samples than loaded samples over a 3-week loading regimen FIG. 10. Specifically, after 1 week of the loading regimen, unloaded samples released more collagen into the medium over the culture time assessed (1-3 weeks). Measurements of hydroxyproline in loaded CTE tissue showed on average about a 12% increase in collagen content over control after 1 week of load, indicating the loading increased the retention or organization of collagen within the biomass.

Figure 11:
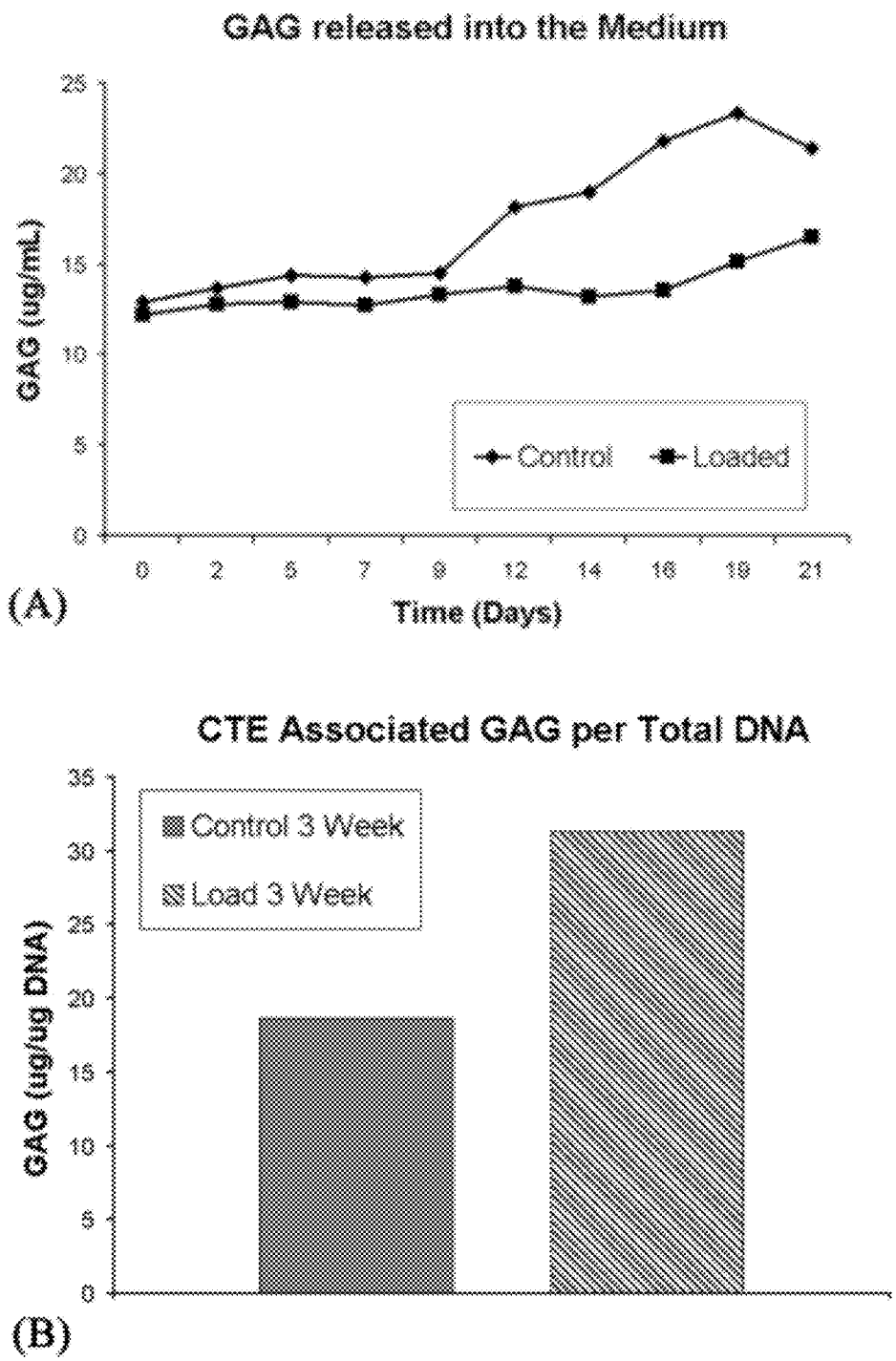
FIG. 11 Panel A is a graph showing the amount of GAG released into the medium by porcine chondrocyte CTEs according to principles of the invention. Panel B is a bar graph showing that the loaded samples incorporated GAG more effectively than control CTEs over time (B).

As with collagen, GAG was released into the medium more in control samples over time FIG. 11, Panel A. After 1 week in the loading regimen, loaded samples demonstrated a decreased GAG level in the medium compared with unloaded controls. When GAG from CTE tissue was measured relative to DNA content, it was determined that about 64% more GAG was incorporated into the matrix per chondrocyte FIG. 11, Panel B. Loaded CTEs more effectively incorporated GAG into the ECM of the growing CTE as a result of loading.

To understand whether chondrocytes were being adversely affected by loading, iNOS gene expression (mRNA) and NO production were studied. iNOS gene expression in chondrocyte CTEs did not differ at any time point, control or loaded (data not shown). The nitrite assay to detect NO release was below the detectable range (in the range of about 0.43 to about 65 µM nitrite) in the medium. These data demonstrate that CTEs benefit from loading without displaying markers of a stressed phenotype, namely, excess NO production and iNOS upregulation.

Figure 12:
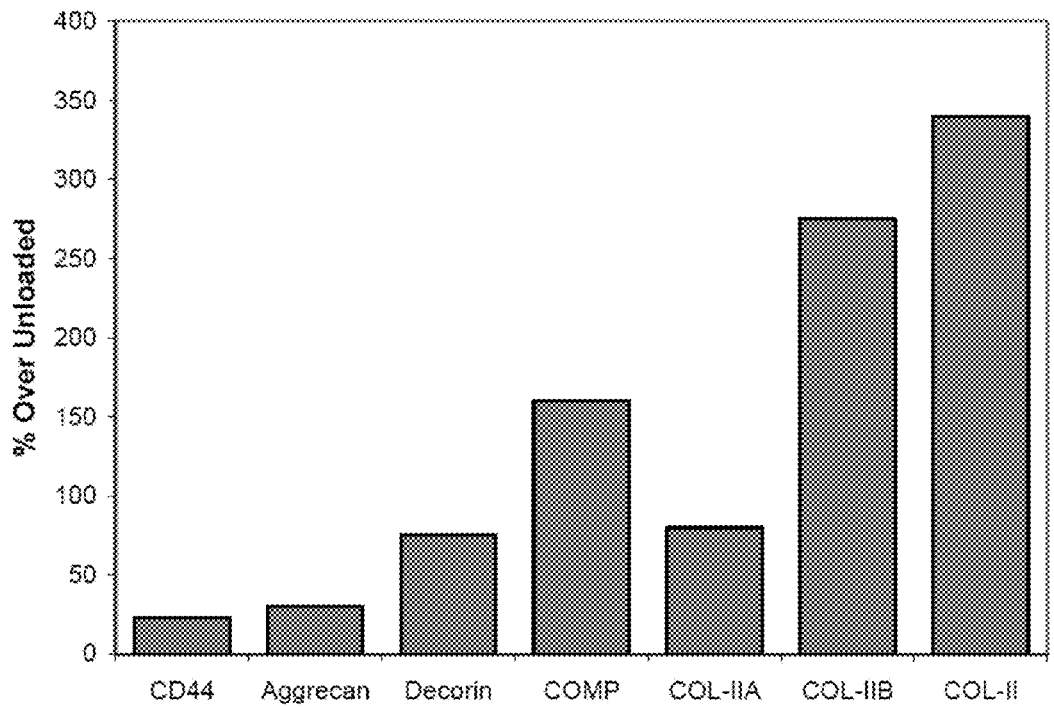
FIG. 12 is a bar chart showing the increased expression of the ECM genes COMP, aggregan, decorin, CD44, and collagen Type IIA and IIB.

Using the suspension culture mode according to principles of the invention, many cartilage-related genes were upregulated when chondrocyte CTEs were loaded for only 1 week. The ECM genes COMP, aggrecan, decorin, and collagen type IIA and IIB as well as a chondrocyte membrane protein, CD44, were all increased in expression levels as shown in this representative experiment FIG. 12.

Figure 13A:
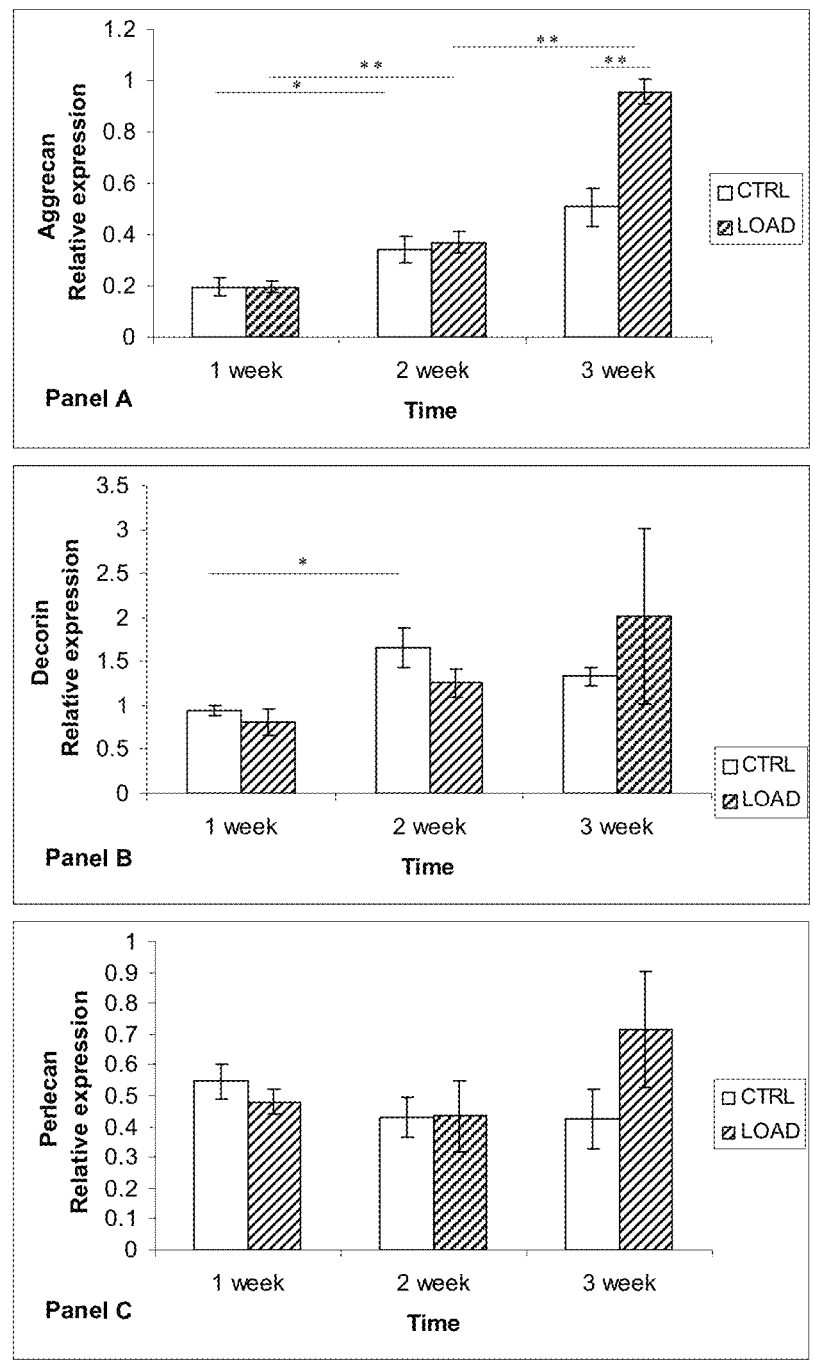
FIG. 13A-B are bar graphs showing up-regulation of the ECM-specific genes in response to load in comparison to unloaded samples according to principles of the invention.
Figure 13B:
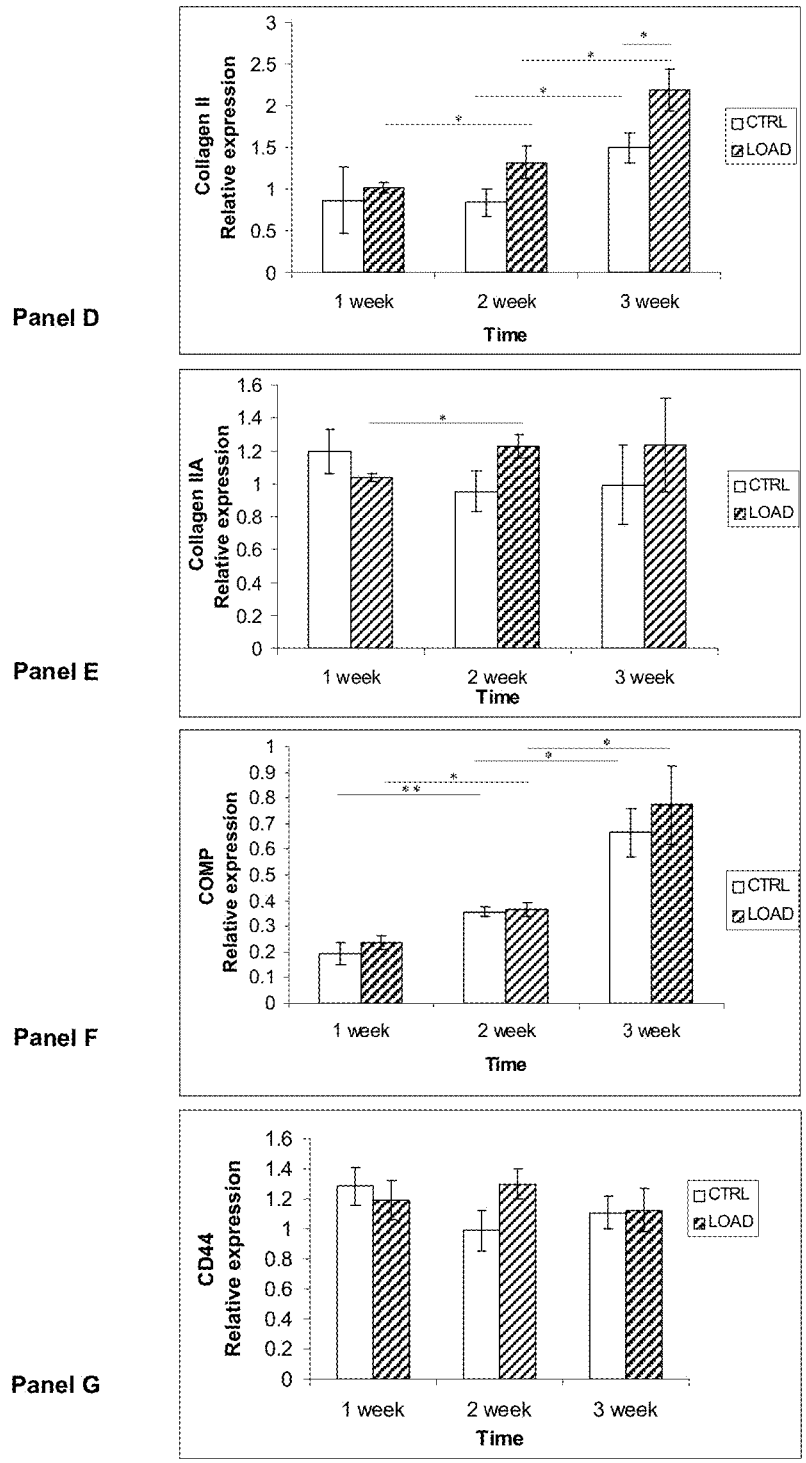

Subsequent experiments focused on how increasing the loading regime can further increase expression levels. Chondrocyte CTEs were loaded for 1 to 3 weeks, with three, 3-hour loading sessions each week. Gene expression in loaded CTEs displayed an overall upregulation of ECM components including collagen type II, aggrecan, COMP, perlecan, and collagen type IIA. Collagen II and aggrecan showed the most dramatic increase in expression in response to loading for 3 weeks, and both were significant ($p<0.05$ and $p<0.01$, respectively) FIGS. 13A-13B. CD44 and collagen type II expression increased near significance ($p<0.07$) after 2 weeks of loading. Since GAG and collagen II were shown to be incorporated into the CTE ECM instead of excreted into medium in this culture model, these data confirm a real increase in aggrecan and collagen type II gene expression by mechanical pressure non-adherent, self-aggregating suspension culture increased expression of COMP, collagen type II, and aggrecan significantly over time, regardless of loading.

Specific Example 3

Effect of Loading on Mesenchymal Stem Cells in Control Medium

Figure 14:
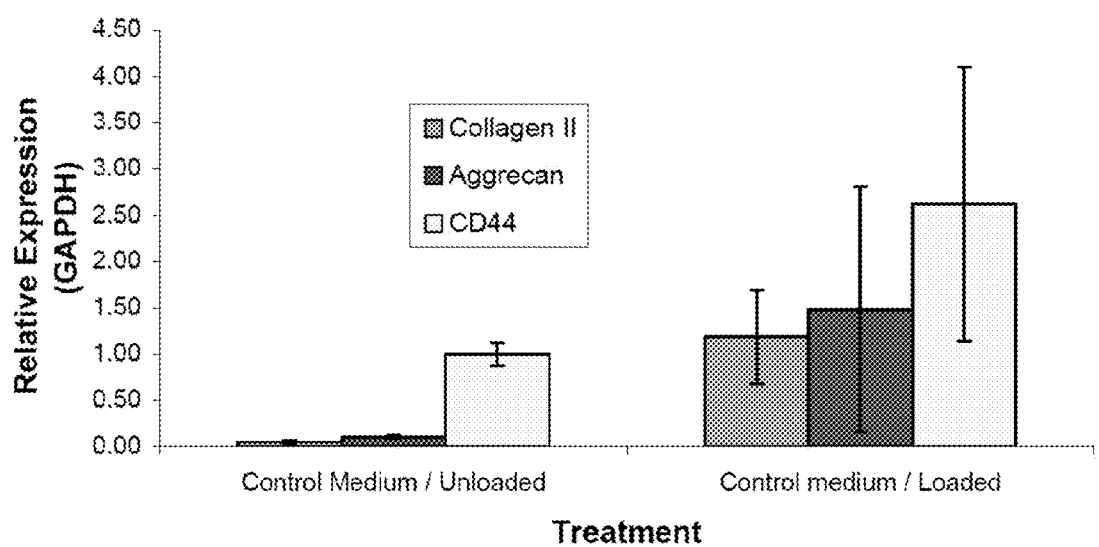
FIG. 14 is a bar graph showing the relative expression collagen Type II, aggregan and CD44 in MSC cultured in control medium in loaded and unloaded samples according to principles of the invention.

The object of this example was to determine the effect of loading on human mesenchymal stem cells (HMSC) cultured in non-differentiation medium (control medium) and chondrogenic medium after one week of preconditioning. Loading of cells for one week (three sessions) after preconditioning in control medium for one week showed a slight increase in relative expression of ECM components such as collaged type II, aggregan, and CD44 (FIG. 14). Loading for one week after one week of preconditioning in suspension culture showed potential to induce chondrogenesis, even in control medium.

Specific Example 3

Preconditioning Studies on Mesenchymal Stem Cells Prior to Load

Figure 15:
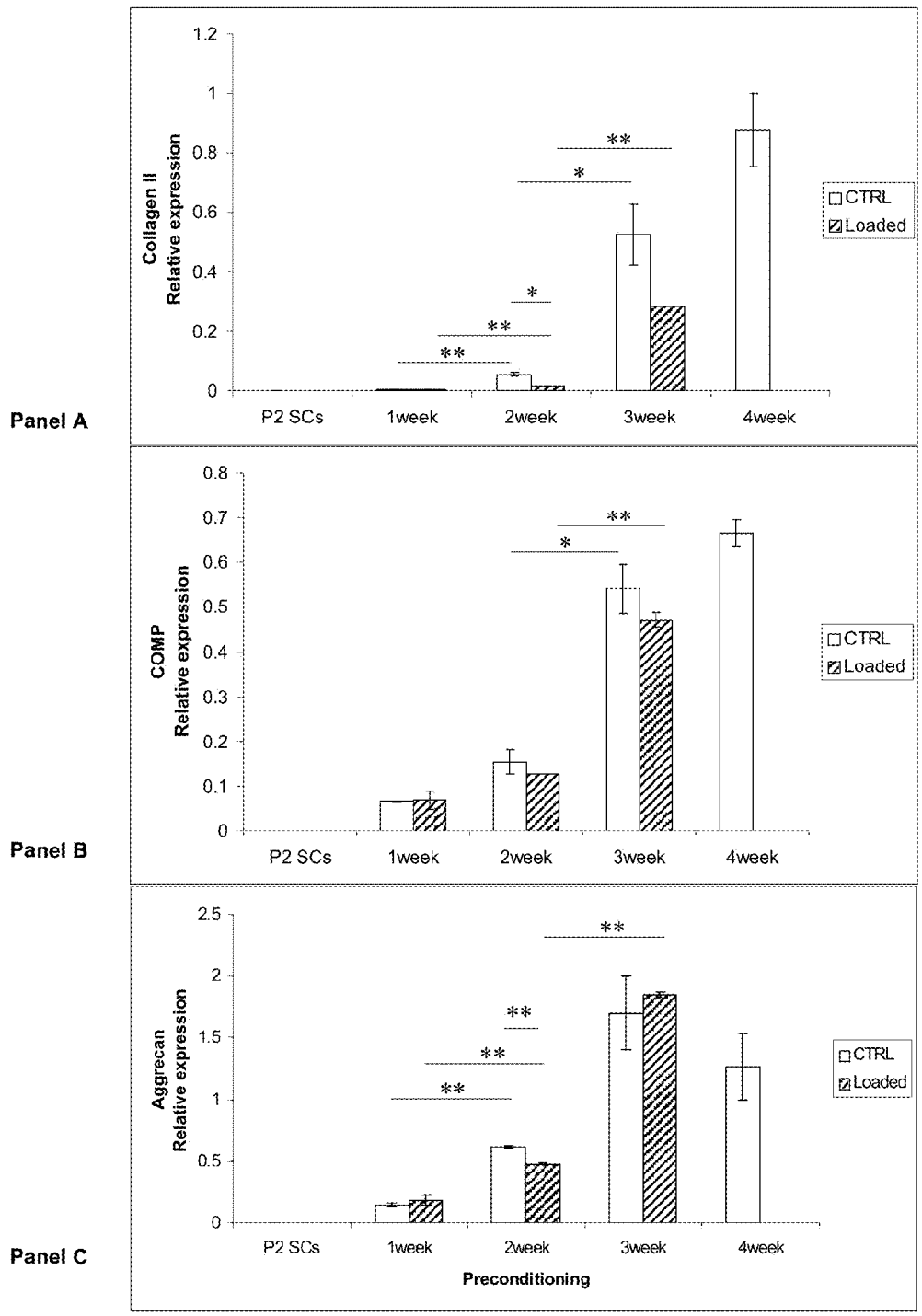
FIG. 15 shows bar graphs of the relative mRNA expression levels of the chondrogenic markers. Panels A-C are bar graphs showing the relative expression levels of collagen type II, COMP, and aggrecan in response to load following preconditioning at different times, respectively.

This example examined the effects of preconditioning the MSCs in CM prior to load. During the preconditioning period the cells slowly accumulated ECM responded more favorably to load, as shown in FIG. 15. As seen in FIG. 15, aggrecan expression increased in response to loading after three weeks of preconditioning in CM.

Figure 16:
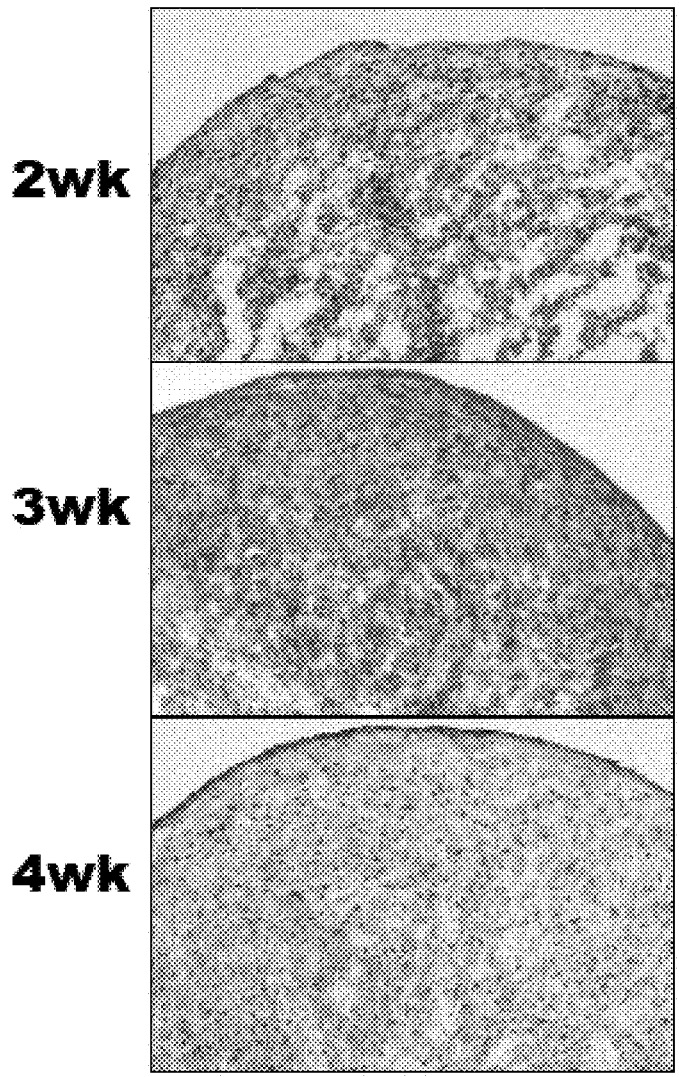
FIG. 16 are micrographs at 20× original magnification of equine MSC CTE samples according to principles of the invention stained in hemotoxylin and eosin preconditioned for 2 weeks, 3 weeks, and 4 weeks. The micrographs show that the CTEs become more densely packed and organized with each week in preconditioning culture.

With each week of preconditioning samples became more densely packed and appeared more organized FIG. 16. There was also an overall increase in uniformity across the biomass with each week of culture in CM. Uniformity was seen as similar cell arrangements and consistent spacing between individual cells (composed of matrix). The gaps that were seen in sections were not artifacts of the sectioning procedure, however, they were seen throughout the many different sections. These gaps in the matrix were likely the result of the shorter culture time and the CTE producing less ECM components. The gaps present at 1 week preconditioning samples (not shown) and 2 week preconditioning samples disappear at 3 and 4 week samples. Accordingly, the more time in culture the more dense the ECM appeared in histological sections.

Figure 17:
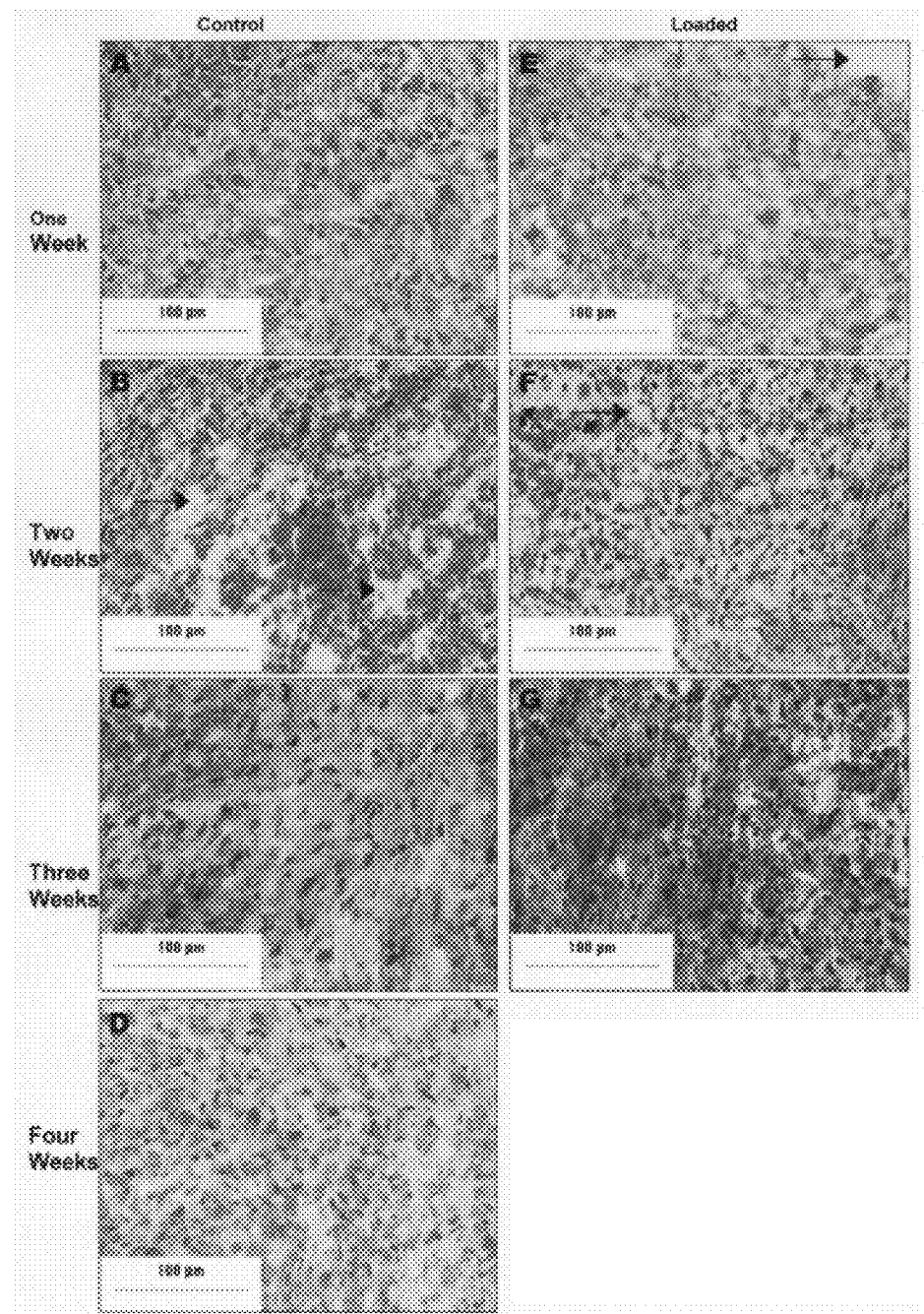
FIG. 17 are micrographs of MSCs preconditioned for 1 week (Panel A and Panel E), 2 weeks (Panel B and Panel F), 3 weeks (Panel C and Panel G) and 4 weeks (Panel D) according to principles of the invention. Duration in culture showed a large accumulation of ECM and a more densely packed CTE. Samples from 1 week of preconditioning had not fully self-aggregated into a sphere and images are shown of regions that filled the viewing space. Load CTEs (Panels E, F, And G) showed a higher cell-to-matrix ratio.

MSC biomasses were examined histologically by staining with hematoxylin and eosin in order to determine the cell-to-matrix ratio or cell density. At identical magnification, three representative sections of each biomass were photographed and nuclei counted (40× original magnification). The cell-to-matrix ratio was determined using the average cell number within the viewing frame. This method gave a good estimate of cell number within a defined area as well as an idea of the accumulation of matrix and progress towards a cartilage-like phenotype. There were visible changes from week to week of preconditioning FIG. 17, Panels A-D. Moreover, the application of load also changed the cell density FIG. 17, Panels E-G. As shown by the arrows in FIG. 17, Panels B, E, and F, preconditioning reduced the presence of gaps in the matrix, and increased the accumulation of a densely packed ECM.

Figure 18:
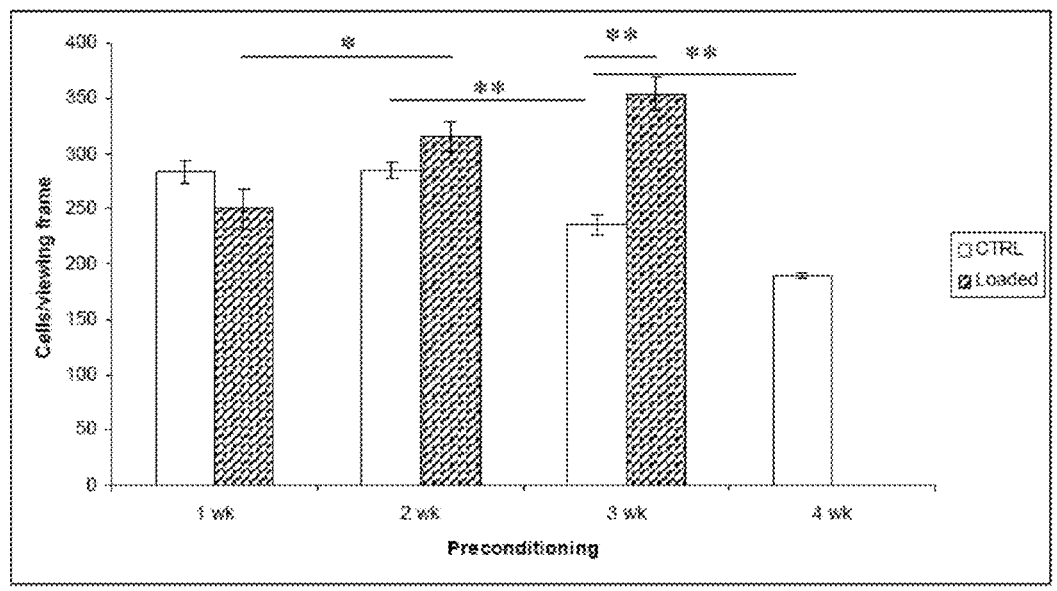
FIG. 18 is a bar graph showing the cell-to-matrix ratio (cell density) of MSC preconditioned for a varying times in loaded and unloaded samples according to principles of the invention.
Figure 19:
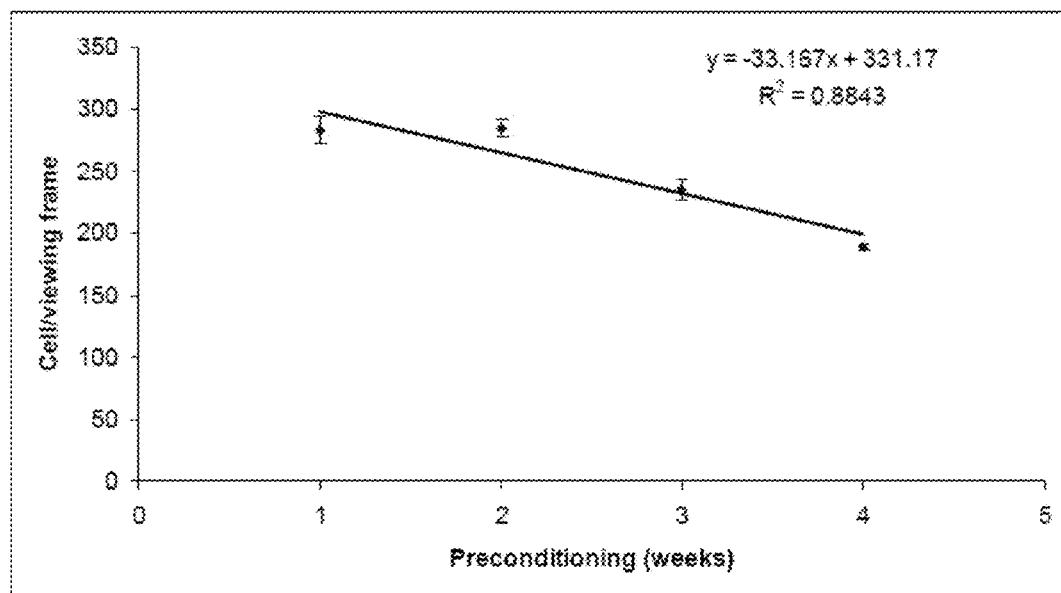
FIG. 19 is a graph showing a decrease in the cell-to-matrix ratio and accumulation of ECM MSC CTEs (unloaded) with time in culture according to principles of the invention.

Cell-to-matrix data is represented as cells per viewing frame. MSC biomass samples had cells in the range of about 187 cells to about 371 cells per viewing frame in comparison to adult human cartilage isolated from the femoral condyle had cells in the range of about 5 cells to about 10 cells per viewing frame. Preconditioning of the CTEs significantly decreased the cell-to-matrix ratio over time, specifically from week about 2 to about week 4 FIG. 18. The accumulation of matrix between cells could be seen in the images taken of the CTEs (FIG. 17) and, as shown in FIG. 19, followed a linear decrease in cell-to-matrix ratio ($R^2=0.8834$). The decreasing size of error bars with each increasing week demonstrated increased uniformity and organization in the CTE FIG. 19.

Specific Example 4

Biomechanical Testing of CTEs

Biomechanical tests on CTEs using a uniaxial confined compression stress-relaxation protocol were performed. Material properties were calculated using theory based on the experimental protocol from the literature. Cultured tissue equivalents were taken immediately from their culture environment for testing. The mechanical tests were performed using a materials testing machine (Instron Corp., Canton, Me.). Each specimen was placed in a confined compression chamber and submerged in a bath filled with phosphate buffer solution.

Samples were allowed 15 minutes to reach equilibrium under an initial tare load of 0.0854 N. Five 7.5% compressive stain increments were then applied at a rate of 2.5 N/m-s with the displacement was held constant for 1400 seconds between them. Cartilage mechanical properties were described using linear, biphasic theory. The aggregate modulus and the hydraulic permeability were solved.

Figure 20:
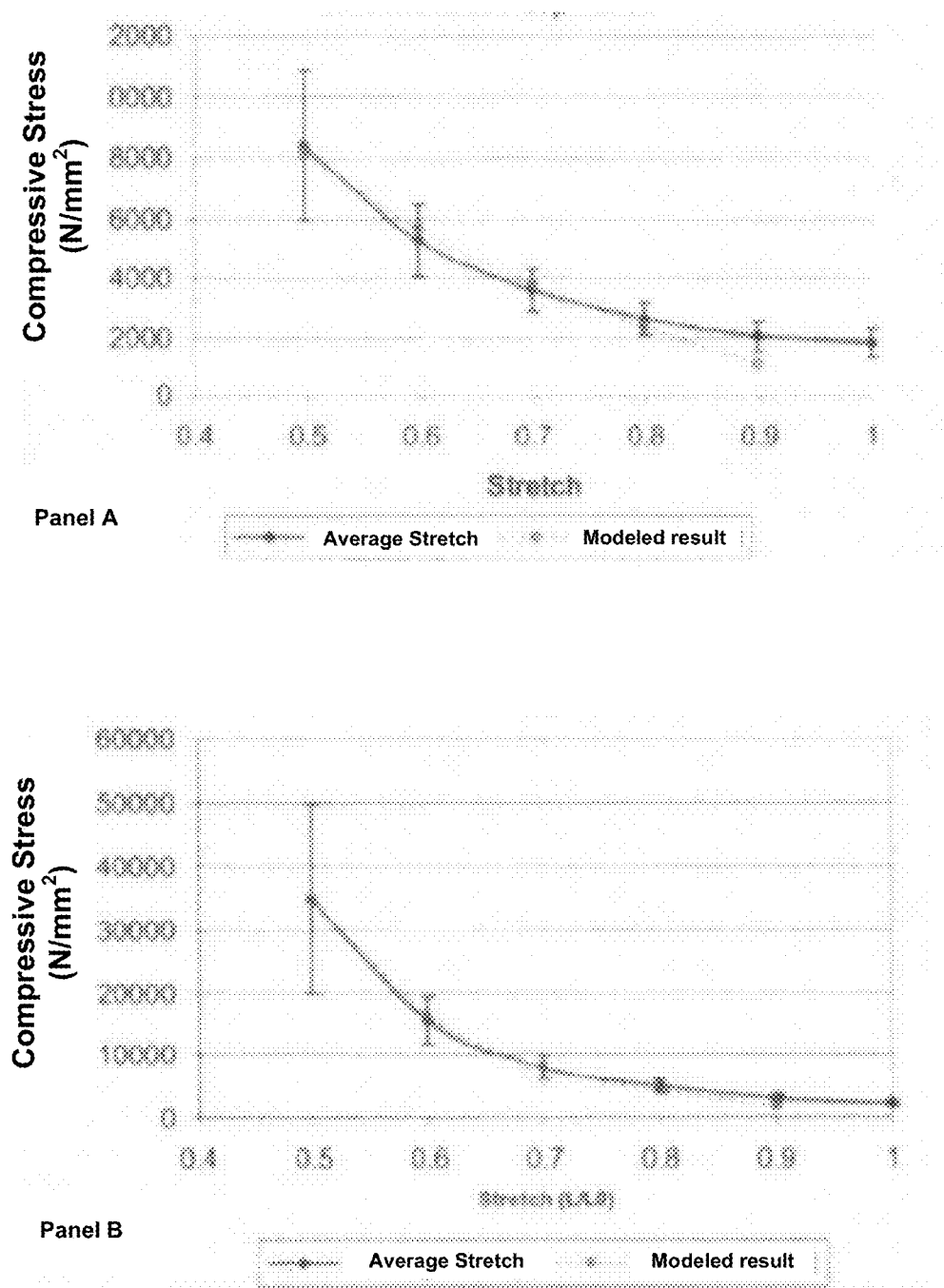
FIG. 20 are graphs showing the stress relaxation equilibrium. Panel A shows the average equilibrium compressive stress values with standard deviations for the lower group of material responses from 1 to about 0.5 of stretch or 50% compression. Panel B shows the average equilibrium compressive stress values with standard deviations for the higher group of material responses. The average moduli for the low stress group was $H_{AO}$=10.120 kPa and the average moduli for the high stress group was $H_{AO}$=16.07 kPa.

Seventeen five mm diameter specimens were tested from six different CTE culture. Each CTE was of equal to or greater than about 10 weeks in culture. Care was made to take representative samples from various locations on the thickened rim of the CTE in an effort to have regions that might differ due to their structural appearance. FIG. 20, Panels A and B demonstrate the results of equilibrium stress versus stretch. Of the two data group noted, thirteen behaved at a lower level of stress and four that achieved higher levels of stress (FIG. 20, Panels A and B, respectively). Those with higher stress were specifically taken from areas of the CTE that appeared thicker and more dense. FIG. 20, Panel A shows the average equilibrium compressive stress values with standard deviations (n=13) for the lower group of material responses from 1 to 0.5 of stretch, or 50% compression, and FIG. 20, Panel B for the higher group (n=4). The aggregate moduli for the low stress group was $H_{AO}=10.120$ kPa and for the high stress group $H_{AO}=16.07$ kPa.

A second group of CTE samples underwent mechanical testing after 8 and 16 weeks in culture. Five mm diameter specimens with an average thickness of about 2.886 (0.304) mm for the eight week specimens and about 2.914 (0.269) mm for the sixteen week specimens were punched out of the CTE samples. A Student's t-test was performed to identify significant differences between the material properties of the samples from the eight week and sixteen week culture times with p<0.05. For comparison to the cultured CTE, six cartilage explants were also tested from the native pig tissue from which chondrocytes were isolated. The aggregate modulus and permeability for the eight week specimens were about 0.0416 (SD 0.0043) MPa and about 2.85E-13 (SD 2.45E-13) $m^4$/Ns respectively. The sixteen week CTE specimens had an aggregate modulus and permeability of about 0.0352 (0.0076) MPa and about 2.67E-13 (SD 1.06E-13) $m^4$/Ns respectively.

Figure 21:
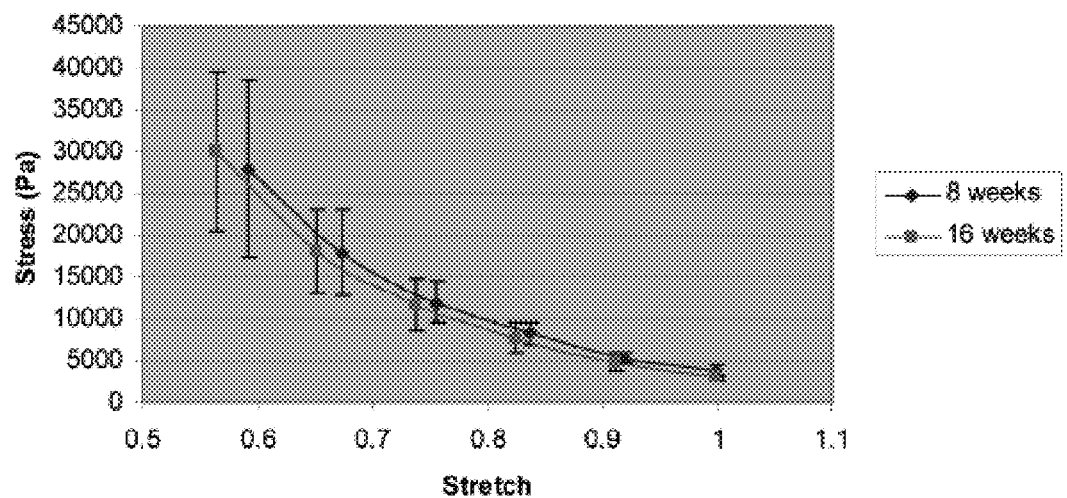
FIG. 21 is a graph showing the results of equilibrium stress versus stretch for the two specimen groups.

The theoretical model corresponded to the analytical solution with correlation coefficients ($R^2$) for the eight week CTE specimens and was about 0.946 (SD 0.044) and for the sixteen week CTE specimens was about 0.900 (SD 0.041). A trend toward a significant difference was found in the aggregate modulus between the two culture times (p<0.1). No significant difference was found in the permeability between culture times. FIG. 21 demonstrates the results of equilibrium stress versus stretch for the two specimen groups. For comparison, cartilage plugs from the knee of one fetal pig femoral condyle had an average equilibrium aggregate modulus of about 229.6 kPa.

Specific Example 5

Comparison of Load CTEs and Unload CTEs

An in vitro loading experiment was performed on the ability of cyclic loading, for about 3 hours, about 3 days a week with a magnitude of in a range of about 0.1 MPa to about 5 MPa, to positively affect the biological and mechanical outcome measures. Eight CTE specimens were separated into two groups, the unloaded control group and the loaded group. The control specimens remained under the same culture conditions, while the loaded CTE specimens were 'exercised' over a 3-week period.

Four loaded CTE specimens were placed in a four-well plate and vacuum-sealed with polyurethane bags to protect the CTE from contamination and to minimize the gas compression during pressurization. The sealed wells were then placed in a pressure chamber and filled with hydraulic fluid. The pressure chamber was sealed, closed, and the remaining air within the chamber was extracted. A 2.5 kip hydraulic piston (Miller, Bensenville, Ill.) was mounted onto a materials testing machine (Instron Corp., Canton, Me.) which compressed the piston and pressurized the chamber. Cyclical loading in a range of about 0.5 MPa to about 5.0 MPa was applied for about 3 hours at a frequency of about 0.1 Hz. The process was repeated on Mondays, Wednesdays, and Fridays for 3 weeks. Prior to and after loading, a media sample was saved for analysis of collagen and PG expression changes and the medium was replaced. CTEs were kept in an incubator until the next loading period.

Following the completion of the hydrostatic loading regimen, both loaded and control CTE specimens underwent biochemical and mechanical analysis. Biological analysis of CTEs that were cyclically loaded to an unloaded control is first presented. Expression of extracellular matrix genes (ECM) was markedly affected by this loading regimen. Molecules secreted into the medium during culturing and loading were analyzed. Also RNA, DNA, and proteins of the CTE at the end of the 3 weeks were also tested.

Figure 22:
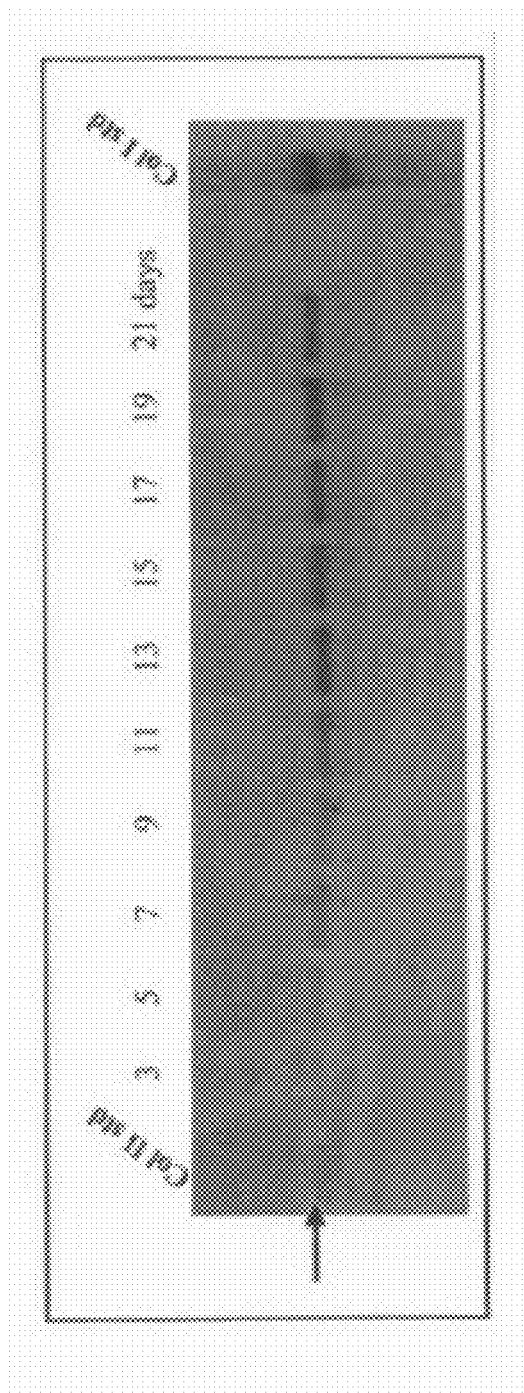
FIG. 22 is a picture of a Commassie blue stained SDS-PAGE gel of pepsin-digested media sampled after the culture period following loading according to principles of the invention. There is an increase in type II collagen over time.

The study of the medium enabled detection of the secreted proteins that accumulated during the 2 or 3 days following load, and served to demonstrate that the constitutive proteins were biosynthesized, such as type II collagen and aggrecan. FIG. 22 is a photograph of a Commassie blue stained SDS-PAGE of pepsin-digested media sampled after the culture period following loading. In this representative CTE (loaded) there is an increase with time of collagen type II ($\alpha_1$(II) chain indicated with arrow) synthesized during the 3 week period and no evidence of type I collagen expressed (note: the small band beneath the ($\alpha_1$(II) chain is a degradation product of type II typically seen and furthermore is not the size of the ($\alpha_1$(I) chain indicated by standard). In regard to the secreted type II collagen profile, the unloaded control is not noticeably different. In the analysis of CTE tissue itself, differences in the two groups are marked, particularly for the mRNA of critical ECM genes.

The amount of GAG (an accepted measure of proteoglycan) in the medium was tested during the 3-week culture and in the CTE at the end. Loading resulted in a greater degree of organization within the CTE. There was more GAG in the loaded CTE as compared to the unloaded CTE. GAG released into the medium (not organize into the CTE) was higher in the unloaded control. The amount of DNA in each CTE tested was similar although the GAG data was standardized using the DNA content.

The mRNA for collagen and aggrecan in the CTE were all up-regulated as a result of loading. RNA was prepared from a set of CTE and analyzed using PCR, followed with real-time PCR. cDNA was prepared from 1.0 µg with iScript and manufacturers' recommendations followed by PCR using Amplitaq-Gold and standard procedures, including a 59° C. annealing temperature. Cycle times were optimized by removing samples every 5 cycles and the PCR products were digitized using image analysis software (Alpha Imager). The data were standardized using values for GAP PCR products. RNA from loaded CTE had greater than about 240% more aggrecan expression and about a 136% increase in type II collagen expression using this PCR approach. Using real-time PCR (BioRad icycler MyiQ), these observations were followed-up with real-time analysis.

Using the real-time analysis (using the BioRad Expression analysis software Macro) aggrecan was increased by about 1.56±0.241 (std. dev.) fold (56%) in the loaded CTE as compared to the expression of aggrecan mRNA in the unloaded CTE. Collagen type II was increased by about 1.63+0.762 fold (63%) over control unloaded CTE. Real-time PCR was performed using perlecan specific primers previously shown to be specific for the porcine sequence. The relative expression of perlecan was striking with about a 2.03+0.256 fold increase and was highly significant (p=0.0001).

Loaded chondrocyte cultures were also tested for presence of CD44. CD44 mRNA levels increased in a range of about 45% to about 63% in loaded cultures when compared to unloaded cultures. Together these data clearly show that loading for a short regimen of about 3 weeks at physiologically relevant levels, ECM genes and molecules can be affected in a positive manner.

The mechanical test that used for the study described in this example was the one dimensional confined compression incremental stress relaxation testing as described in the examples above. The aggregate modulus of the control and loaded specimens were about 15.1 kPa (0.86 SD) and about 21.1 kPa (3.85) respectively, about a 40% increase with loading. The permeability was found to be about $10.5 \times 10^{-13}$ $m^4$/Ns ($9.4 \times 10^{-13}$) for the control specimens and about $1.27 \times 10^{-13}$ $m^4$/Ns ($0.56 \times 10^{-13}$) for the pressurized specimens, about an 88% decrease. Although the small specimen numbers precluded statistical comparisons, however, the results show more cartilage-like behavior in loaded specimens compared to the unloaded specimens.

Specific Example 6

Characterization of CTE and Comparison to Native Cartilage

Figure 23:
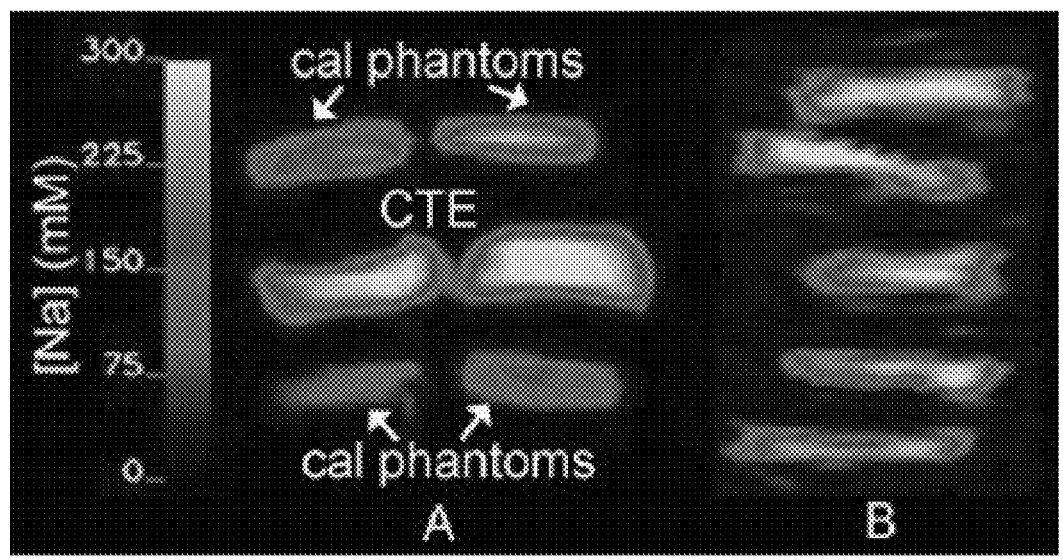
FIG. 23 shows a photograph of two CTE produced according to principles of the invention generated by sodium MRI.

Multiple CTE each of 10 weeks in culture were analyzed. FIG. 23 provides a representative image of two CTE FIG. 23, a comparison of sodium data of a CTE (FIG. 23, Panel A) and an ex vivo porcine patella (FIG. 23, Panel B). The adjacent barscale in FIG. 23 corresponds to the pixels in the map to sodium concentration.

Next, the intrinsic properties of the CTE were measured using MRI. Sodium concentration was measured as an indicator of proteoglycan content in the tissue. Sodium MRI images of the CTE were collected and a spatial "map" of sodium concentration was calculated from the MRI data. The data were compared with similar data collected on patellar cartilage from a porcine animal model FIG. 23, Panel B. The similar sodium concentrations indicate that the proteoglycan content of the CTE is similar to that of the porcine patella. The sodium maps of two representative CTE samples and five representative ex vivo bovine patellar cartilage explants of approximately the same dimensions are shown. Average sodium concentrations of the CTE were about 260±30 mM and about 278±46 mM, respectively. For comparison, the average sodium concentration of bovine explants was in the range of about 300±40 mM. The similar sodium concentrations indicate that the fixed charge density (FCD) and hence proteoglycan content of the CTE samples were similar to that of bovine patellae.

Figure 24:
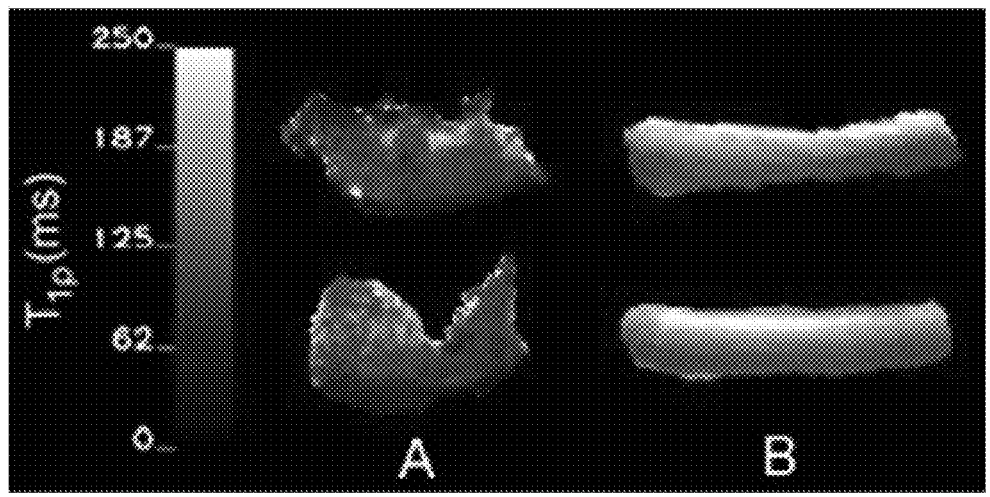
FIG. 24 shows photographs of the $T_{1p}$ MRI generated maps of CTE samples produced according to principles of the invention.

$T_{1p}$ maps of the same CTE samples and two representative bovine cartilage explants are shown in FIG. 24. It can be observed in FIG. 24, Panel A from the $T_{1p}$ maps that the CTE samples are more heterogeneous than the bovine cartilage explants FIG. 24 Panel B. However the CTE have the consistent feature of lower $T_{1p}$ near the base and higher $T_{1p}$ near the surface. However, they lack the same degree of structural organization observed in the bovine samples with well-defined superficial and middle zones with high and low $T_{1p}$, respectively. The average $T_{1p}$ of the CTE samples was about 105±9 ms and about 107±14 ms, respectively. These values are similar to the average $T_{1p}$ of bovine cartilage which is typically in the range of about 110±10 ms.

The CTE specimens produced using the methodology of the invention have characteristics comparable native tissue and similar or improved in comparison to other previously reported materials. The compressive stiffness of the CTE obtained by the methodology of the invention is either similar to that found in other studies or an improvement. Measurements of sodium content and $T_{1p}$ via MRI are similar to those of bovine cartilage indicating that the CTE has similar compositional properties, particularly with regard to proteoglycan content.

The MRI-based methods offer the advantages of providing noninvasive, nondestructive, and quantitative surrogate measures of material properties. These techniques may be used to monitor characteristics of CTE samples in future studies where the gene expression of constitutive matrix genes by molecular and biomechanical approaches may be modified.

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled molecular biology or in the relevant fields are intended to be within the scope of the appended claims.

The disclosures of all references and publications cited above are expressly incorporated by reference in their entireties to the same extent as if each were incorporated by reference individually.

---

What is claimed is:

1. A method for producing a cartilage-like biomaterial, said method comprising the steps of:
   a) culturing cells at a density of at least about $1\times10^6$ cells/mL in a culture media in suspension;
   b) maintaining the cells in suspension for a period of time without the use of any physical support or cell attachment; and
   c) applying a mechanical force to the cells at an effective pressure, for a period of time, so as to form a cartilage-like biomaterial;
   wherein the cells are not cultured in monolayer culture prior to step a), and wherein the cells are maintained in suspension throughout the entire method.

2. The method of claim 1, further comprising the step of seeding the cells into a culture apparatus containing the culture media prior to said culturing step.

3. The method of claim 1, wherein the step of maintaining the cells in suspension involves preconditioning the cells for a period of time prior to applying the mechanical force.

4. The method of claim 3, wherein the period of time of said preconditioning from about 1 week to about 10 weeks.

5. The method of claim 4, wherein the period of time of said preconditioning is about 8 weeks.

6. The method of claim 1, wherein the cells provided for said culturing step are undifferentiated cells.

7. The method of claim 6, wherein the undifferentiated cells are mesenchymal stem cells.

8. The method of claim 6, wherein the culture medium comprises chondrogenic media.

9. The method of claim 6, wherein the culture media comprises complete media.

10. The method of claim 1, wherein the cells provided for said culturing step are differentiated cells.

11. The method of claim 10, wherein the media comprises complete media.

12. The method of claim 10, wherein the differentiated cells are chondrocytes.

13. The method of claim 1, wherein the mechanical force in said applying step is selected from the group consisting of cyclical dynamic loading, dynamic shearing, and hydrostatic loading.

14. The method of claim 13, wherein the hydrostatic loading is cyclical hydrostatic pressure.

15. The method of claim 1, wherein the effective pressure of said mechanical force in said applying step is in a range of about 0.5 MPa to about 1.0 MPa.

16. The method of claim 1, wherein the mechanical force in said applying step is applied intermittently.

17. The method of claim 16, wherein intermittently comprises applying the mechanical force about 3 times per week for a time period of about 3 hours each time.

18. The method of claim 1, wherein the mechanical force in said applying step is applied for a period of time ranging from about 1 week to about 10 weeks.

19. The method of claim 1, wherein the culture media is augmented with a chondrogenic factor.

20. The method of claim 19, wherein the chondrogenic factor is selected from the group consisting of BMP-2, BMP-4, chondrogenic stimulating activity factor (CSA), TGF-β, IL-1, IL-6, IL-8, insulin-like growth factor 1 (IGF-1), fibroblast growth factors (FGF), prostaglandins, vascular endothelial growth factor (VEGF), platelet-derived growth factor (PDGF), perlecan and a fragment thereof, miniperl and a fragment thereof, chondroitin sulfate, glucosamine, glucosamine sulfate, dexamethasone, insulin, transferrin and sodium selenite (ITS), and combinations thereof.

21. The method of claim 1, wherein the culture media is augmented with a biologically active agent.

22. The method of claim 21, wherein the biologically active fragment is one or more compounds selected from the group consisting of naphthoquinone, tocopherol, tocotrienol, ergocalciferol, cholecalciferol, ascorbic acid, cyanocolbalamin, folic acid, biotin, pyridoxine, pantothenic acid, niacin, riboflavin, thiamine, retinoids, carotenoids, minerals, iron, calcium, magnesium, zinc, copper, selenium, iodine, chromium, potassium, manganese, glucosamine, glucosamine sulfate, and combinations thereof.

23. The method of claim 1, wherein the cartilage-like biomaterial expresses type II collagen.

24. The method of claim 1, wherein the biomaterial minimally expresses type I collagen, or expresses collagen Type I in an undetectable level.

25. A method of producing cartilage-like biomaterial, said method comprising the steps of:
a) culturing a high density suspension of cells without physical support for cell attachment; and
b) applying a cyclical hydrostatic load to the cells at an effective pressure and for a period of time effective to produce the cartilage-like biomaterial;
wherein the cells are not cultured in monolayer culture prior to step a), and wherein the cells are maintained in suspension throughout the entire method.

26. The method of claim 25, wherein the cells provided for said culturing step are primary culture cells.

27. The method of claim 26, wherein the primary culture cells are mesenchymal stem cells.

28. The method of claim 25, wherein the cells provided for said culturing step are chondrocytes.

29. The method of claim 25, wherein the density of cells provided for said culturing step is in a range of about $1 \times 10^6$ cells/mL to about $1 \times 10^8$ cells/mL.

30. The method of claim 25, wherein the cells provided for said culturing step have a capacity to self-aggregate and form a biomass.

31. The method of claim 25, wherein the cyclical hydrostatic load in said applying step is applied continuously or intermittently.

32. The method of claim 31, wherein the intermittent application of the cyclical hydrostatic force involves applying the hydrostatic force about 3 times per week for a time period of about 3 hours each time.

33. The method of claim 25, wherein the culturing step involves culturing the cells for a time period in the range of about 1 week to about 10 weeks.

34. The method of claim 25, further comprising the step of preconditioning the cells for a time period in the range of about 1 week to about 4 weeks prior to applying the cyclical hydrostatic load to the cells.

35. The method of claim 25, wherein the cells in said culturing step are cultured in a chondrogenic medium augmented with a chondrogenic factor.

36. The method of claim 35, wherein the chondrogenic factor is one or more factors selected from the group consisting of BMP-2, BMP-4, chondrogenic stimulating activity factor (CSA), TGF-β, IL-1, IL-6, IL-8, insulin-like growth factor 1 (IGF-1), fibroblast growth factor (FGF), prostaglandins, vascular endothelial growth factor (VEGF), platelet-derived growth factor (PDGF), perlecan and a fragment thereof, miniperl and fragment thereof, chondroitin sulfate, glucosamine, glucosamine sulfate, dexamethasone, insulin, transferrin and sodium selenite (ITS), and combinations thereof.

* * * * *

SEQUENCE LISTING

```
<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: PCR amplification primer designed around
      nucleotide 144 of alternatively spliced heparan
      sulfate proteoglycan (HSPG2, perlecan) variant
      miniperl, "Primer No. 144"

<400> SEQUENCE: 1
gtgacccatg ggctgagggc ata                                            23

<210> SEQ ID NO 2
<211> LENGTH: 19
<212> TYPE: DNA
<213> ORGANISM: Artificial Sequence
<220> FEATURE:
<223> OTHER INFORMATION: PCR amplification primer designed around
      nucleotide 659 of alternatively spliced heparan
      sulfate proteoglycan (HSPG2, perlecan) variant
      miniperl, "Primer No. 659"

<400> SEQUENCE: 2
```

```
gggcactgtg cccaggcgt                                              19

<210> SEQ ID NO 3
<211> LENGTH: 20
<212> TYPE: DNA
<213> ORGANISM: Artificial Sequence
<220> FEATURE:
<223> OTHER INFORMATION: perlecan specific PCR amplification primer
      designed around nucleotide 353 of alternatively
      spliced heparan sulfate proteoglycan (HSPG2,
      perlecan) variant miniperl, "Primer No. 353"

<400> SEQUENCE: 3
tcgctccatc gagtacagcc                                             20

<210> SEQ ID NO 4
<211> LENGTH: 21
<212> TYPE: DNA
<213> ORGANISM: Artificial Sequence
<220> FEATURE:
<223> OTHER INFORMATION: PCR amplification primer designed around
      nucleotide 677 of alternatively spliced heparan
      sulfate proteoglycan (HSPG2, perlecan) variant
      miniperl, "Primer No. 677"

<400> SEQUENCE: 4
gcaggctctt gggaactggg g                                           21

<210> SEQ ID NO 5
<211> LENGTH: 24
<212> TYPE: DNA
<213> ORGANISM: Artificial Sequence
<220> FEATURE:
<223> OTHER INFORMATION: PCR amplification primer designed around
      nucleotide 1 of alternatively spliced heparan
      sulfate proteoglycan (HSPG2, perlecan) variant
      miniperl, "Primer No. 1"

<400> SEQUENCE: 5
acttccagat ggggagctgg atgg                                        24
```